US005672722A

United States Patent [19]

Seto et al.

[11] Patent Number: 5,672,722

[45] Date of Patent: Sep. 30, 1997

[54] COLOR FADE INHIBITOR

[75] Inventors: Nobuo Seto; Yasuhiro Yoshioka; Masakazu Morigaki, all of Minami-ashigara, Japan

[73] Assignee: Fuji Photo Film Co., Ltd., Kanagawa, Japan

[21] Appl. No.: 478,769

[22] Filed: Jun. 7, 1995

Related U.S. Application Data

[63] Continuation-in-part of Ser. No. 337,472, Nov. 8, 1994, abandoned.

[30] Foreign Application Priority Data

Nov. 12, 1993 [JP] Japan .................................. 5-305999

[51] Int. Cl.$^6$ ...................... C07D 311/64; C07D 307/79; C07D 311/58

[52] U.S. Cl. .......................... 549/398; 549/408; 549/462

[58] Field of Search .................................. 549/398, 408, 549/462

[56] References Cited

U.S. PATENT DOCUMENTS 3,432,300 3/1969 Lestina et al. .
4,782,011 11/1988 Goddard et al. .
5,294,530 3/1994 Seto et al. .

OTHER PUBLICATIONS

Sorrell et al., J. Org. Chem., 50, 5765–5769 (1985).

*Primary Examiner*—Nicky Chan
*Attorney, Agent, or Firm*—Birch, Stewart, Kolasch & Birch, LLP

[57] ABSTRACT

A silver halide color photographic material comprising a support having thereon at least one layer containing at least one compound represented by formula (A)

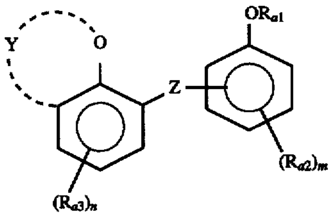

(A)

wherein the definition of $R_{a1}$, $R_{a2}$, $R_{a3}$, Z, Y, m and n is described in the specification.

6 Claims, No Drawings

COLOR FADE INHIBITOR

This application is a continuation-in-part of application Ser. No. 08/337,472 filed on Nov. 8, 1994, now abandoned, the entire contents of which are hereby incorporated by reference.

FIELD OF THE INVENTION

The present invention relates to a silver halide color photographic material and, more particularly to a silver halide color photographic material capable of giving color images having an improved fastness without causing color turbidity.

BACKGROUND OF THE INVENTION

A silver halide color photographic material generally has silver halide emulsion layers sensitive to the three primary colors of red, green, and blue and by a so-called subtractive color process, i.e., a process of coloring each of the three kinds of couplers in the silver halide emulsion layers in the relation of a complementary color with the color sensitive to each emulsion layer, color images are formed.

The color images obtained by photographic processing the silver halide color photographic material are generally composed of azomethine dyes or indianiline dyes formed by the reaction of the oxidation product of an aromatic primary amine color developing agent and couplers.

The color images thus obtained are not always stable to light, humidity, and heat and hence when the color images are exposed to light for a long period of time or stored under the conditions of a high temperature and a high humidity, the color images are faded or discolored to deteriorate the color images.

Such fading and discoloring of color images are a defect which can be said to be a fatal defect for a recording material. As a method of removing such a defect, the development of couplers giving dyes having a high fastness, the use of fading inhibitors, the use of ultraviolet absorbents for preventing the deterioration of color images by ultraviolet rays, etc., have been proposed.

In these proposals, the effect of inhibiting the deterioration of images with a fading inhibitor is large. For this purpose, it is known to add hydroquinones, hindered phenols, catechols, gallic acid esters, aminophenols, hindered amines, chromanols, indanes, the ethers or esters obtained by silylating, acylating, or alkylating the phenolic hydroxy groups of the foregoing compounds, and further metal complexes, etc.

However, these compounds may certainly have the effect as an inhibitor of the fading and discoloring of color images but the effect obtained by these compounds is yet insufficient for meeting the requirement by customers who require a higher image quality. Also, some of these compounds greatly color the background portions, cause coloring (hereinafter, is referred to as fog) at unexposed portions, cause coloring hindrance of couplers, and also cause color turbidity by forming dyes by causing a reaction with the oxidation product of a color developing agent as color development to give bad influences on the photographic characteristics. Thus, these are not satisfactory compounds. Furthermore, some of these compounds cause inferior dispersion or form fine crystals after coating the emulsion thereof, and hence they have not yet given generally excellent effects for color photograph.

Also, the compounds having the structures similar to the chroman structure and coumaran structure or the compounds having a bisphenolic structure are known as an image deterioration inhibitor. These compounds all show a fading inhibition effect. But since they are insufficient for the strong requirement for obtaining fastness of color images. Moreover, some of these compounds color the background to yellow (yellow stain) with the passage of time and form dyes by causing a reaction with the oxidation product of a color developing agent at developing to cause a color turbidity. Therefore, these compounds are not excellent ones.

SUMMARY OF THE INVENTION

An object of the present invention is to provide a color photographic light-sensitive material capable of forming color images which do not discolor for a long period of time and having a high storage stability.

Another object of the present invention is to provide a color photographic light-sensitive material containing a photographic additive which forms neither change of a hue nor fog, does not form dyes by reacting with the oxidation product of a color developing agent at development, does not lower the color density, and has a sufficient effect of inhibiting fading and discoloring color images.

Further object of the present invention is to provide a color photographic material containing a photographic additive which is excellent in the solubility in a high-boiling organic solvent, etc., and does not give bad influences on the coloring property of dye-forming couplers and on other photographic additives.

Still another object of the present invention is to provide a color photographic material having a high storage stability containing a photographic additive which gives color images formed by coloring of dye-forming couplers, said color images not fading when stored for a long period of time and does not cause coloring (yellow stain) at the background with the passage of time.

As the result of various investigations, the inventors have discovered that the objects described above can be achieved by incorporating at least one of the compounds represented by following formula (A) in a silver halide color photographic material.

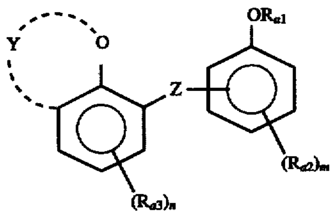

(A)

In the above formula, $R_{a1}$ represents a hydrogen atom, an aliphatic group, an aliphatic acyl group, an arylacyl group, an aliphatic sulfonyl group, or an arylsulfonyl group; $R_{a2}$ represents a substituent; $R_{a3}$ represents an aliphatic group, an aryl group, a carbamoyl group, a sulfamoyl group, an aliphatic oxycarbonyl group, an aryloxycarbonyl group, an aliphatic oxy group, an aryloxy group, an aliphatic thio group, an arylthio group, an aliphatic sulfonyl group, an arylsulfonyl group, an aliphatic amino group, an arylamino group, an aliphatic acylamino group, or an arylacylamino group, an aliphatic oxycarbonylamino group, an aryloxycarbonylamino group, or a halogen atom; Y represents a non-metallic atomic group necessary for forming a 5- or 6-membered ring together with the oxygen atom; Z represents a single bond, an oxygen atom, a sulfur atom, or —$C(R_{a4})(R_{a5})$— (wherein $R_{a4}$ and $R_{a5}$, which may be the same or different, each represents a hydrogen atom, an aliphatic group, or an aryl group); m represents an integer of from 0 to 4; n represents an integer of from 0 to 3, when m and n are each plural, plural $R_{a2}$'s and plural $R_{a3}$'s may be the same or different, and when n is an integer of 2 or 3 and plural $R_{a3}$'s are the ortho-positions with each other, they may combine with each other, with the exclusion that $R_{a1}$ and $R_{a2}$ combine with each other and when m is 2 or more, plural $R_{a2}$'s combine with each other.

DETAILED DESCRIPTION OF THE INVENTION

Then, the invention is described in detail.

The compound represented by formula (A) being used in the present invention is a compound for inhibiting fading of color images formed by couplers and is a non-coloring compound. "Non-coloring compound" means a compound which does not substantially provide a color when processed with a color developing solution.

In addition, unless otherwise indicated, when the group in this invention contains an aliphatic moiety, the aliphatic moiety may be straight chain, branched, or cyclic and may be saturated or unsaturated. For example, the aliphatic moiety represents an alkyl, an alkenyl, a cycloalkyl, or a cycloalkenyl and these aliphatic moieties may be unsubstituted or may have a substituent.

Also, when the group contains an aryl moiety, the aryl moiety may be monocyclic or a condensed ring and may be unsubstituted or substituted.

Furthermore, when the group contains a heterocyclic moiety, the heterocyclic moiety has hetero atom(s) (e.g., a nitrogen atom, a sulfur atom, and an oxygen atom) in the ring, may be a saturated ring or an unsaturated ring, may be monocyclic or a condensed ring, or may be unsubstituted or substituted.

The substituent described in the present specification may be a substitutable group and examples of the substituent are an aliphatic group, an aryl group, a heterocyclic group, an acyl group, an acyloxy group, an acylamino group, an aliphatic oxy group, an aryloxy group, a heterocyclic oxy group, an aliphatic oxycarbonyl group, an aryloxycarbonyl group, a heterocyclic oxycarbonyl group, a carbamoyl group, an aliphatic sulfonyl group, an arylsulfonyl group, an aliphatic sulfonyloxy group, an arylsulfonyloxy group, a sulfamoyl group, an aliphatic sulfonamido group, an arylsulfonamido group, an amino group, an aliphatic amino group, an arylamino group, an aliphatic oxycarbonylamino group, an aryloxycarbonylamino group, an aliphatic sulfinyl group, an arylsulfinyl group, an aliphatic thio group, an arylthio-group, a hydroxy group, a cyano group, a nitro group, a sulfo group, a hydroxyamino group, an aliphatic oxyamino group, an aryloxyamino group, a carbamoylamino group, a sulfamoylamino group, a halogen atom, a sulfamoylcarbamoyl group, and a carbamoylsulfamoyl group.

Then, each group in the formula (A) is explained in detail.

That is, $R_{a1}$ represents a hydrogen atom, an aliphatic group which may have a substituent [preferably, an alkyl group having from 1 to 40 carbon atoms which may have a substituent, e.g., methyl, ethyl, i-propyl, cyclohexyl, benzyl, dodecyl, 2-(2,4-di-t-pentylphenoxy)ethyl, and 2-(butoxycarbonyl)ethyl], or an aliphatic acyl or arylacyl group which may have a substituent (preferably an alkylcarbonyl group having from 2 to 42 carbon atoms which may have a substituent, an alkenylcarbonyl group having from 3 to 42 carbon atoms which may have a substituent, or an arylcarbonyl group having from 7 to 47 carbon atoms which may have a substituent, e.g., acetyl, pivaloyl, myristoyl, benzoyl, 4-t-butylbenzoyl, acryloyl, and methacryloyl), or an aliphatic sulfonyl or arylsulfonyl group which may have a substituent (preferably, an alkanesulfonyl group having from 1 to 40 carbon atoms which may have a substituent or an arylsulfonyl group having from 6 to 46 carbon atoms which may have a substituent, e.g., butanesulfonyl, hexyloxyethylsulfonyl, benzenesulfonyl, and 4-dodecyloxybenzenesulfonyl).

$R_{a2}$ represents a substituent (examples of preferred substituent are an aliphatic group (preferably having from 1 to 40 carbon atoms, e.g., methyl, ethyl, i-propyl, t-butyl, cyclohexyl, benzyl, dodecyl and oleyl), an aryl group (preferably having 6 to 46 carbon atoms, e.g., phenyl, naphthyl, 4-methylphenyl, 2,4-di-t-butylphenyl, 4-myristoylaminophenyl and 3-dodecyloxyphenyl), a heterocyclic group (preferably having from 1 to 46 carbon atoms, e.g., thienyl, furyl, chromenyl, pyridyl, pyrazoyl, chromanyl, morpholinyl and indolyl), an acylamide group (preferably having from 2 to 42 carbon atoms, e.g., acetylamino, pyvaloylamino, stearylamino, oleylamino, benzoylamino and p-dodecylbenzoylamino), a sulfonamide group (preferably having from 1 to 40 carbon atoms, e.g., methanesulfonamide, octadecanesulfonamide, benzensulfonamide, toluenesulfonamide and m-hexadecyloxycarbonylbenzenesulfonamide), a carbamoyl group (preferably having 2 to 47 carbon atoms, e.g., diethylcarbamoyl and N-methyl-N-phenylcarbamoyl ), a sulfamoyl group (preferably having from 1 to 46 carbon atoms, e.g., dibutylsulfamoyl, docdecylsulfamoyl, phenylsulfamoyl and N-octyl-N-phenylsulfamoyl), a carbamoylamino group (preferably having from 2 to 47 carbon atoms, e.g., dioctylcarbamoylamino and phenylcarbamoylamino), an aliphatic oxycarbonyl or aryloxycarbonyl group (preferably having from 2 to 47 carbon atoms, e.g., methoxycarbonyl, hexadecyloxycarbonyl, phenyloxycarbonyl and 2,4-di-t-amylphenoxycarbonyl), an aliphatic oxycarbonylamino or aryloxycarbonylamino group (preferably having from 2 to 47 carbon atoms, e.g., methoxycarbonylamino and phenoxycarbonylamino), an aliphatic oxy or aryloxy group (preferably having from 1 to 46 carbon atoms, e.g., methoxy, ethoxy, cyclohexyloxy, benzyloxy, i-tridecyloxy, stearyloxy, phenyloxy, p-octyloxyphenyloxy and 4-(morpholine-1-yl)phenyloxy), an aliphatic thio or arylthio group (preferably having from 1 to 46 carbon atoms, e.g., methylthio, ethylthio, t-butylthio, dodecylthio, phenylthio and 4-methoxyphenylthio), an aliphatic sulfonyl or arylsulfonyl group (preferably having from 1 to 46 carbon atoms, e.g., butanesulfonyl, cyclohexanesulfonyl, benzensulfonyl and 4-dodecyloxybenzensulfonyl), an aliphatic amino or arylamino group (preferably having from 1 to 46 carbon atoms, e.g., dimethyl amino, methyloctadecylamino, N-methylanilino and 4-methoxyanilino), or a halogen atom (e.g., fluorine, chlorine and bromine)), and these substituents may be, if possible, further substituted.

$R_{a3}$ represents an aliphatic group which may have a substituent (preferably, an alkyl group having from 1 to 40 carbon atoms which may have a substituent, e.g., methyl, ethyl, i-propyl, cyclohexyl, t-butyl, benzyl, dodecyl, methoxymethyl, butylthiomethyl, and phenethyl), an aryl group which may have a substituent (preferably, an aryl group having from 6 to 36 carbon atoms which may have a substituent, e.g., phenyl, 4-methylphenyl, 2,4-di-t-butyl phenyl, 4-myristoylaminophenyl, and 3-dodecyloxyphenyl), a carbamoyl which may have a substituent (preferably, an alkylcarbamoyl group having from 2 to 47 carbon atoms which may have a substituent or an arylcarbamoyl group having from 7 to 47 carbon atoms which may have a substituent, e.g., diethylcarbamoyl and N-methyl-N-phenylcarbamoyl), a sulfamoyl which may have a substituent (preferably, an alkylsulfamoyl group having from 1 to 40 carbon atoms which may have a substituent or an arylsulfamoyl group having from 6 to 46 carbon atoms which may have a substituent, e.g., dibutylsulfamoyl, dodecylsulfamoyl, phenylsulfamoyl, and N-octyl-N-phenylsulfamoyl), an aliphatic oxycarbonyl or aryloxycarbonyl group which may have a substituent (preferably, an alkoxycarbonyl group having from 2 to 42 carbon atoms which may have a substituent or an aryloxycarbonyl group having from 7 to 47 carbon atoms which may have a substituent, e.g., hexyloxycarbonyl, 2-ethylhexyloxycarbonyl, phenoxycarbonyl, and 2,4-di-t-butylphenoxycarbonyl), an aliphatic oxy or aryloxy group which may have a substituent (preferably, an alkoxy group having from 1 to 40 carbon atoms which may have a substituent or an aryloxy group having from 6 to 46 carbon atoms which may have a substituent, methoxy, ethoxy, i-propyloxy, hexadecyloxycarbonyl ethoxy, phenoxy, and 4-methoxyphenoxy), an aliphatic thio or arylthio group which may have a substituent (preferably, an alkylthio group having from 1 to 40 carbon atoms which may have a substituent or an arylthio group having from 6 to 46 carbon atoms which may have a substituent, e.g., methylthio, ethylthio, t-butylthio, dodecylthio, phenylthio, and 4-methoxyphenylthio), an aliphatic sulfonyl or arylsulfonyl group which may have a substituent (preferably, an alkanesulfonyl group having from 1 to 40 carbon atoms which may have a substituent or an arylsulfonyl group having from 6 to 46 carbon atoms which may have a substituent, e.g., butanesulfonyl, cyclohexylsulfonyl, benzenesulfonyl, and 4-dodecyloxybenzenesulfonyl), an aliphatic amino or arylamino group which may have a substituent (preferably, an alkylamino group having from 1 to 40 carbon atoms which may have a substituent or an arylamino group having from 6 to 46 carbon atoms which may have a substituent, e.g., dimethyl amino, methyloctadecylamino, N-methylanilino, and 4-methoxyanilino), an aliphatic acylamino or arylacylamino group which may have a substituent (preferably, an alkylacylamino group having from 2 to 42 carbon atoms which may have a substituent or an arylacylamino group having from 7 to 47 carbon atoms which may have a substituent, e.g., acetamino, pivaloylamino, tetradecanoylamino, benzoylamino, and 4-dodecyloxybenzoylamino), an aliphatic oxycarbonylamino or aryloxycarbonylamino group which may have a substituent (preferably, an alkoxycarbonylamino group having from 2 to 42 carbon atoms which may have a substituent or an aryloxycarbonylamino group having from 7 to 47 carbon atoms which may have a substituent, e.g., methoxycarbonylamino, hexadecyloxycarbonylamino, phenoxycarbonylamino, and 4-t-butylphenoxyamino), or a halogen atom (e.g., fluorine, chlorine, and bromine).

Y represents a non-metallic atomic group necessary for forming a 5- or 6-membered ring together with the oxygen atom. The 5- or 6-membered ring may be a saturated ring or an unsaturated ring and also may have a substituent. The total carbon atom number of the ring is preferably from 3 to 23.

Z represents a single bond, an oxygen atom, a sulfur atom, or —C($R_{a4}$) ($R_{a5}$)—.

In the above formula, $R_{a4}$ and $R_{a5}$, which may be the same or different, each represents a hydrogen atom, an aliphatic group which may have a substituent (preferably, an unsubstituted or substituted alkyl group having from 1 to 20 carbon atoms, e.g., methyl, ethyl, i-propyl, dodecyl, cyclohexyl, and benzyl ) or an aryl group which may have a substituent (preferably having from 6 to 30 carbon atoms, e.g., phenyl and 4-methoxyphenyl).

In the formula (A), m represents an integer of from 0 to 4 and n represents an integer of from 0 to 3. When m and n are plural, plural $R_{a4}$'s and $R_{a5}$'s may be the same or different.

Also, when n is an integer of 2 or more and plural $R_{a3}$'s are at the ortho-position with each other, they may combine with each other. However, $R_{a1}$ and $R_{a2}$ do not combine with each other and when m is plural, plural $R_{a2}$'s do not combine with each other.

In the present invention, $R_{a1}$ is preferably a hydrogen atom or an aliphatic group and more preferably a hydrogen atom. $R_{a2}$ is preferably an aliphatic group or an acylamino group, more preferably an aliphatic group (preferably having from 1 to 16 carbon atoms, more preferably from 1 to 8 carbon atoms, e.g., methyl, i-propyl, n-propyl, t-butyl and cyclohexyl), and most preferably an alkyl group (e.g., methyl). $R_{a3}$ is preferably an aliphatic group (preferably having from 1 to 16 carbon atoms, more preferably from 1 to 8 carbon atoms, e.g., methyl, ethyl, n-propyl i-propyl and t-butyl) and more preferably an alkyl group (e.g., methyl). in the case of Y, it is preferred that the ring-forming atomic group is a carbon atom group. In particular, it is preferred that Y forms a coumaran ring or a chroman ring with the oxygen atom and a benzene ring and it is most preferred that Y forms a chroman ring with the oxygen atom. Z is preferably a sulfur atom or —C($R_{a4}$)($R_{a5}$)—, more preferably —C($R_{a4}$)($R_{a5}$)—, and most preferably —CH($R_{a5}$)—. In this case, $R_{a5}$ is preferably a hydrogen atom or an aliphatic group (preferably having 1 to 16 carbon atoms, more preferably 1 to 12 carbon atoms, e.g., methyl, ethyl, i-propyl), more preferably an aliphatic group, far more preferably an alkyl group, and most preferably a branched alkyl group (e.g., i-propyl).

It is more preferred from the point of the effect of the present invention that the compound shown by the formula (A) is the case of the compound shown by following formula (A–I).

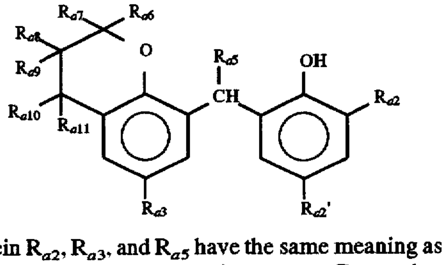
(A-I)

wherein $R_{a2}$, $R_{a3}$, and $R_{a5}$ have the same meaning as defined for the formula (A) , $R_{a2'}$, is same as $R_{a2}$ and examples thereof include the above preferred examples for $R_{a2}$, $R_{a3}$ and $R_{a5}$, and $R_{a6}$, $R_{a7}$, $R_{a8}$, $R_{a9}$, $R_{10}$, and $R_{11}$, which may be the same or different, each represents a hydrogen atom or an alkyl group and the alkyl group having from 1 to 10 carbon atoms (e.g., methyl, ethyl, i-propyl, n-propyl ) is preferred.

Then, specific examples of the compound shown by the formula (A) or (A–I) being used in the present invention but the compounds being used in this invention are not limited to these compounds.

(A-1)
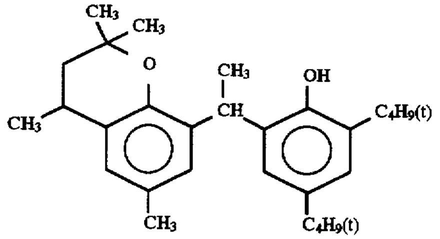
(A-2)
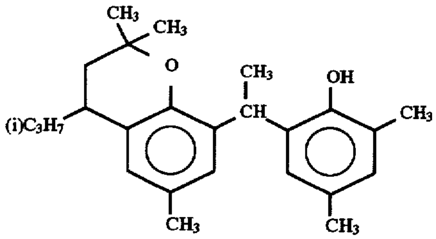
(A-3)
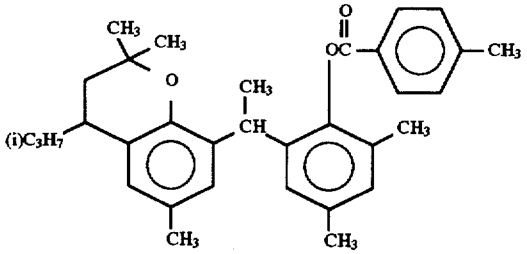
(A-4)
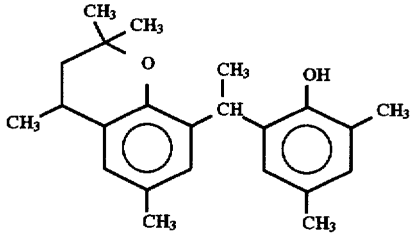
(A-5)
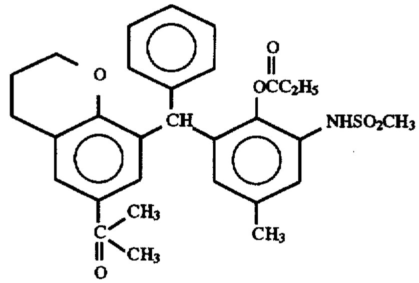
(A-6)
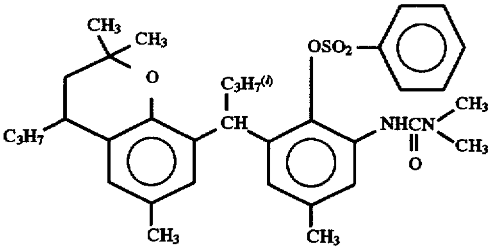
(A-7)
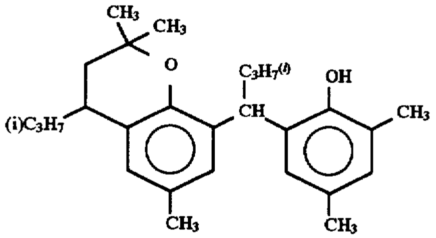
(A-8)
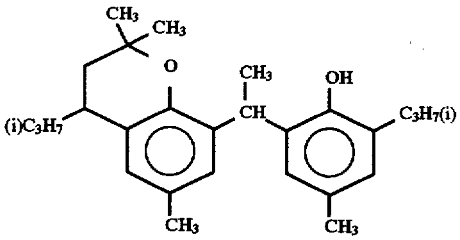
(A-9)
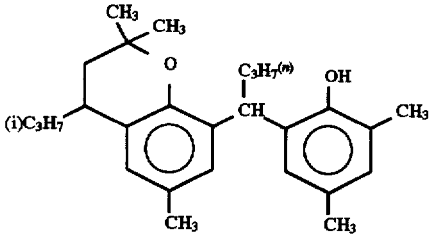
(A-10)
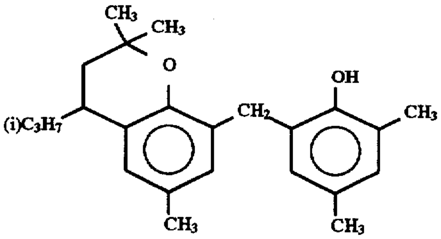
(A-11)
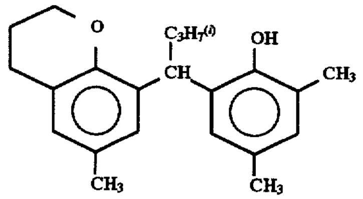
(A-12)
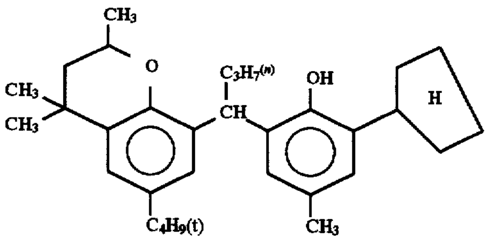

-continued
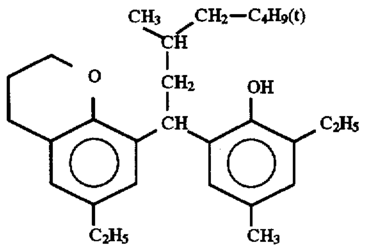
(A-13)
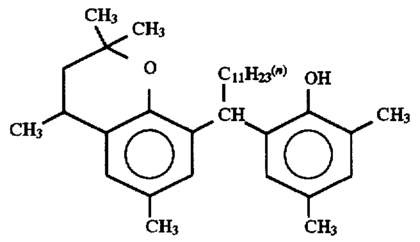
(A-14)
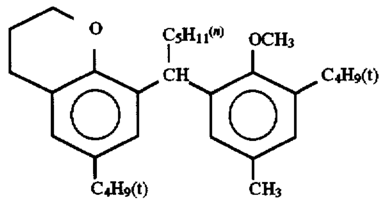
(A-15)
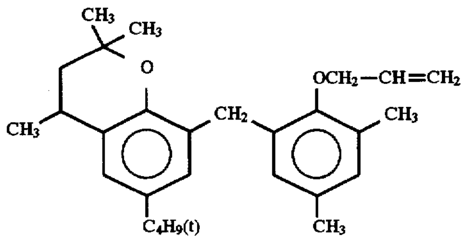
(A-16)
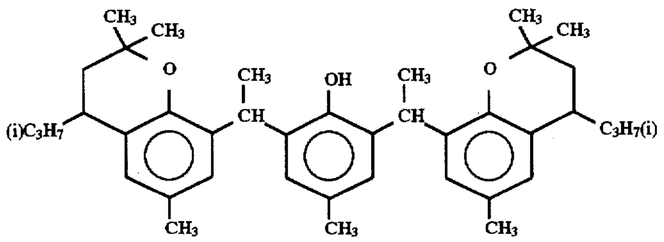
(A-17)
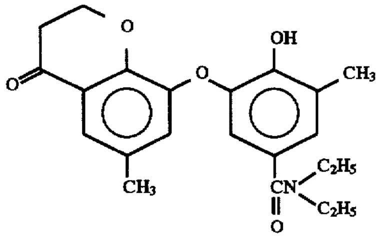
(A-18)
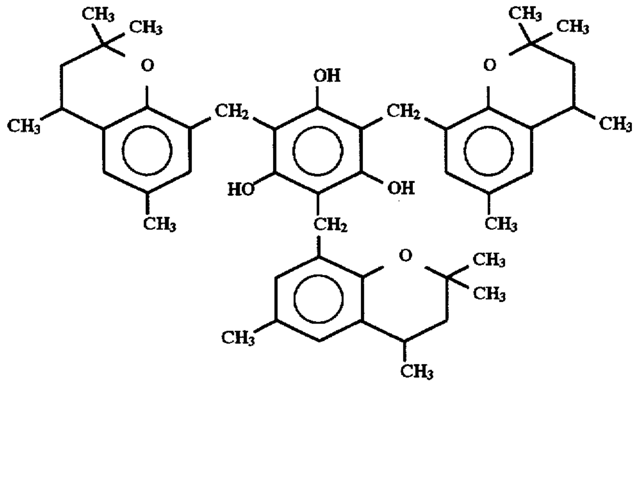
(A-19)

-continued
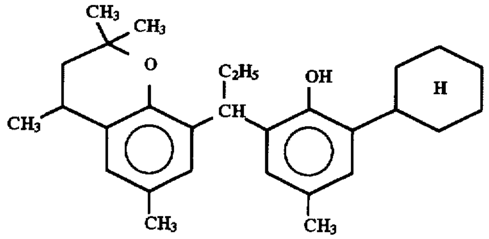
(A-20)
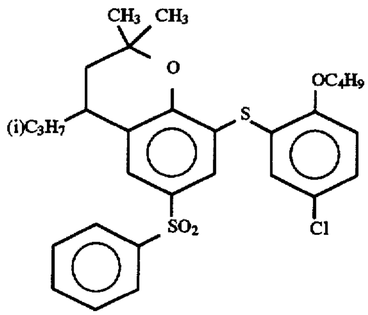
(A-21)
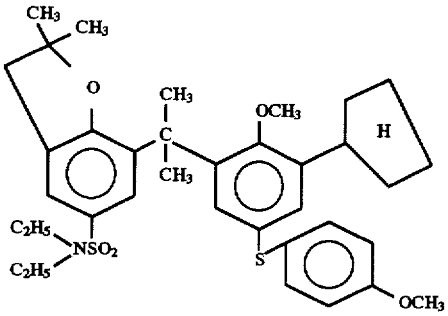
(A-22)
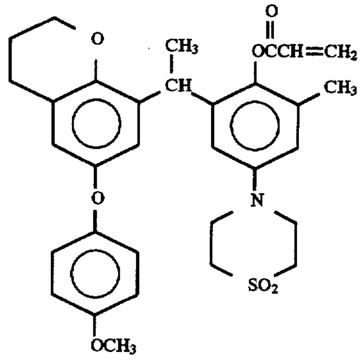
(A-23)
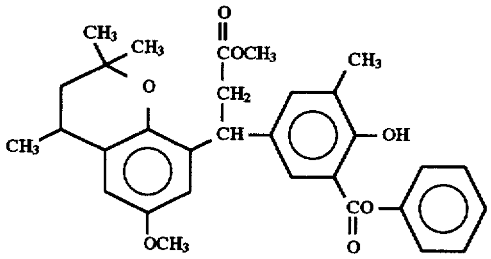
(A-24)
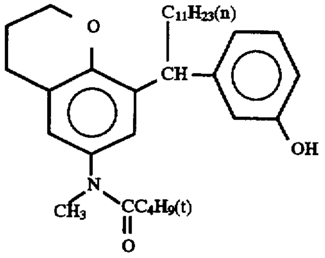
(A-25)
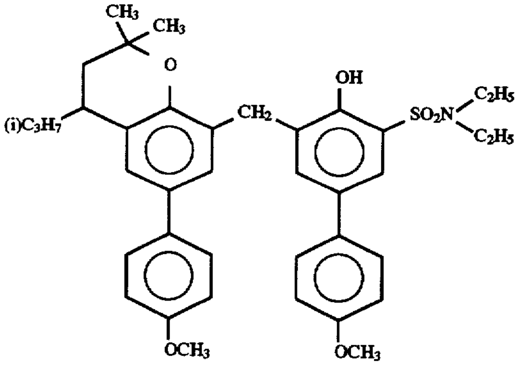
(A-26)
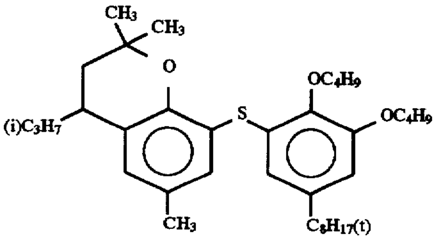
(A-27)
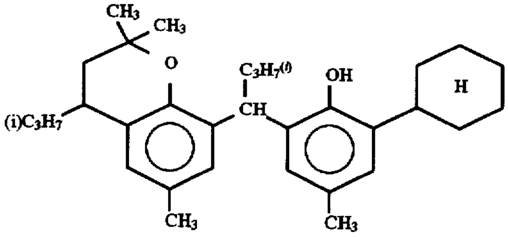
(A-28)
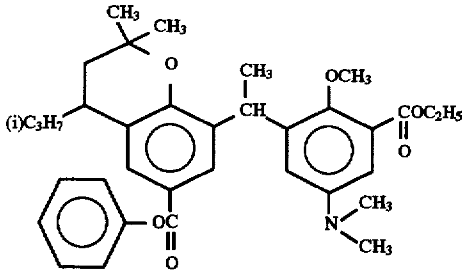
(A-29)

-continued
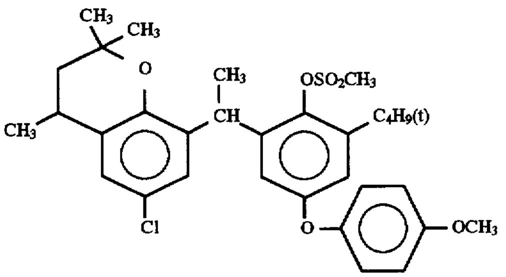
(A-30)
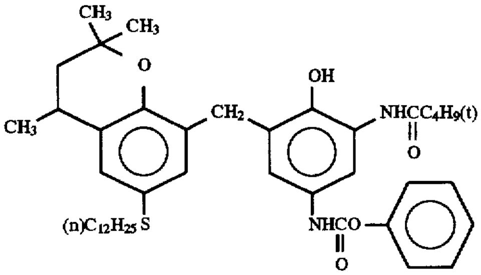
(A-31)
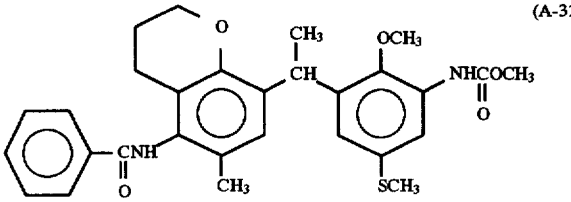
(A-32)
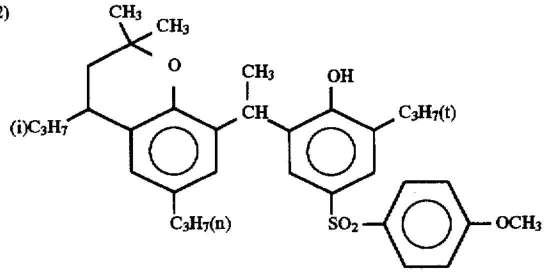
(A-33)
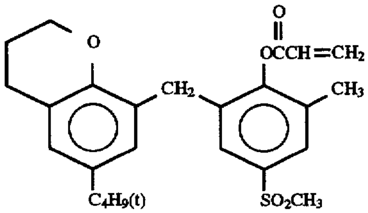
(A-34)
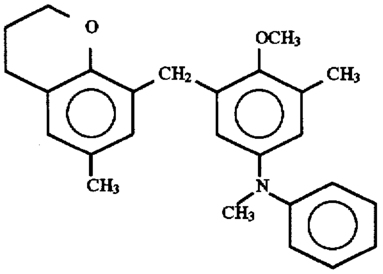
(A-35)
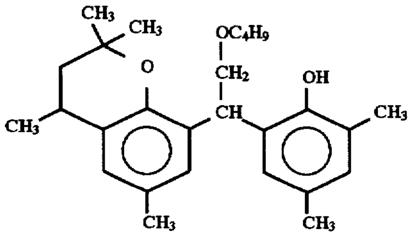
(A-36)
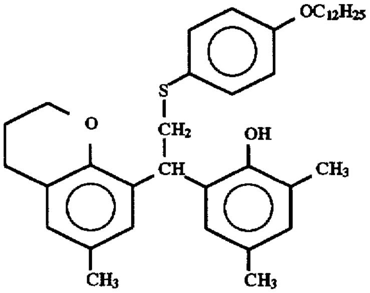
(A-37)
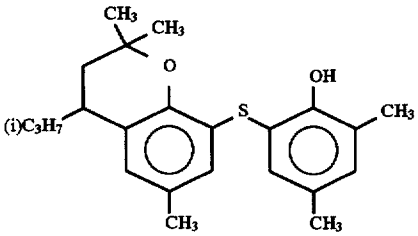
(A-38)
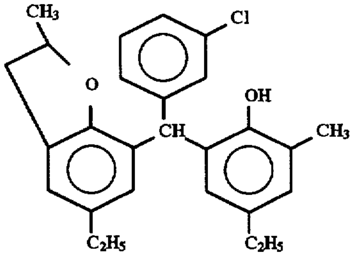
(A-39)

-continued (A-40)

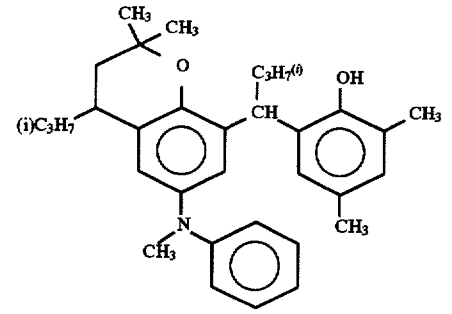

(A-41)

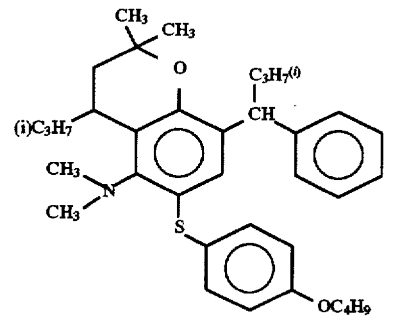

Of them, Compounds (A-1), (A-2), (A-4), (A-7), to (A-14) are preferred.

The compounds shown by formula (A) being used in the present invention can be synthesized by the methods described in U.S. Pat. Nos. 4,782,011 and 3,432,300, PCT WO 91/11749, PCT WO 91/8515, JP-A-50-6338, JP-A-50-87326, JP-A-53-126, etc., (the term "JP-A" as used herein means an "unexamined published Japanese patent application") or the methods similar to the aforesaid methods.

Concretely, a method wherein a substituent corresponding to the linkage group Z is introduced to either

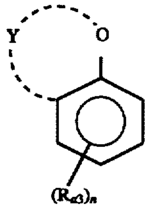

(A)

or

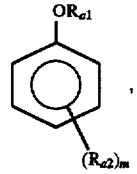

(B)

, and then (A) and (B) are connected by e.g., dehydration-condensation reaction may be used for preparing the compound shown by formula (A).

Then, synthesis examples of the typical compounds are shown below.

SYNTHESIS EXAMPLE 1

Synthesis of Compound (A -2)

To 44 g of 2-acetyl-4,6-dimethylphenol were added 250 ml of ethanol, 4.4 g of palladium carbon (5%), and the mixture was stirred in a 500 ml-volume autoclave in an atmosphere of 75 kg/cm$^2$ of hydrogen gas, at a temperature of 60° C. for 3 hours. After cooling, the reactant solution was filtrated, and ethanol was distilled off under reduced pressure. The residue was crystallized with n-hexane to provide 35.0 g of white crystals (2,4-dimethyl -6-(1-hydroxyethyl) phenol) having a melting point of from 75° to 79° C. with a yield of 79.5%.

To a mixture of 16 g of 2,2,6-trimethyl-4-isopropylchroman and 12 g of the above 2,4-dimethyl-6-(1-hydroxyethyl)phenol was added 20 ml of acetic acid and the resultant mixture was stirred at a temperature of from 20° C. to 23° C. To the mixture was added dropwise 0.2 ml of concentrated sulfuric acid over a period of 5 minutes, thereafter, the temperature was raised to from 25° C. to 30° C., and the mixture was stirred for 3 hours. The reaction mixture obtained was poured into 200 ml of cold water and extracted with 250 ml of an ethyl acetate ester. The ethyl acetate ester layer obtained was washed twice with 250 ml of an aqueous saturated sodium chloride solution, and after drying with anhydrous magnesium sulfate, the solvent was distilled off under reduced pressure. The residue formed was purified with a silica gel column chromatography to provide a viscous colorless liquid (intermediate). The oily material obtained was crystallized with 50 ml of n-hexane to provide 17.7 g of white crystals having a melting point of from 115° C. to 117° C. with a yield of 66.0%.

SYNTHESIS EXAMPLE 2

Synthesis of Compound (A-10)

By following the same procedure as the synthesis method of the compound (A-2) described above except that 11 g of 2,4-dimethyl-6-hydroxymethylphenol was used in place of 12 g of 2,4-dimethyl-6-(1-hydroxyethyl)phenol , the oily product of the compound (A-10) was obtained. The oily product was crystallized with 40 ml of acetonitrile to provide 19.2 g of white crystals having a melting point of from 126° C. to 127° C. with a yield of 75.6%.

SYNTHESIS EXAMPLE 3

Synthesis of Compound (A-7)

To a mixture of 13 g of 2,2,6-trimethyl-4-i-propylchroman and 6.5 g of isobutyrylchloride was added 8.3 g of aluminium chloride for 20 minutes. After stirring for 10 minutes, the reaction mixture was poured into 100 ml of cold water and extracted with 100 ml of an ethylacetate ester. The ethyl acetate ester layer was washed twice with 100 ml of an aqueous saturated sodium chloride solution, and after drying with anhydrous magnesium sulfate, the solvent was distilled off under reduced pressure. To the oily product were added 20 ml of isopropyl alcohol, 20 ml of tetrahydrofuran and 2.5 g of sodium boron hydride and the mixture was subjected to reflux for 4 hours. The reactant solution was poured into 100 ml of cold water and extracted with 100 ml of ethyl acetate ester. The ethyl acetate ester layer was washed twice with 100 ml of an aqueous saturated sodium chloride solution, and after drying with anhydrous magnesium sulfate, the solvent was distilled off under reduced pressure.

To the oily product thus obtained was added 7.2 g of 2,4-dimethylphenyl, and then added 0.5 ml of concentrated sulfuric acid with stirring at a temperature of 20 to 25° C. Further, after stirring for 1 hour, the reactant solution was poured into 100 ml of ethyl acetate ester. The ethyl acetate ester layer was washed twice with 100 ml of an aqueous saturated sodium chloride solution, and after drying with anhydrous magnesium sulfate, the solvent was distilled off under reduced pressure. The residue formed was purified with a silica gel column chromatography to provide a viscous colorless liquid. The oily material obtained was crystallized with 50 ml of n-hexane to provide 12.3 g of white crystals having a melting point of from 98° to 99° C. with a yield of 52.7%. The white crystal was confirmed to be exemplified compound (A-7) with mass spectrum, NMR spectrum and infrared absorption spectrum.

In the silver halide color photographic material of the present invention, at least one layer on the support contains at least one kind of the compounds shown by the formula (A) being used in the present invention. The layer containing the compound of the formula (A) is preferably a silver halide emulsion layer containing a coupler.

The compound shown by the formula (A) being used in the present invention is used in an amount of preferably from 0.0002to 20 g, and more preferably from 0.001 to 5 g per square meter of light-sensitive material. Also, the amount of the formula (A) to the amount of the coupler differs according to the kind of the coupler but is suitably used in the range of from 0.5 to 300 mole %, and preferably from 1 to 200 mole % to a coupler (preferably, the coupler used in the same layer containing the compound).

The compound shown by the formula (A) being used in the present invention may be used together with a known fading inhibitor and in this case, the fading inhibition effect is further increased. Similarly, two or more kinds of the compounds shown by the formula (A) may be used in the present invention.

The compound shown by the formula (A) being used in the present invention is preferably used with a compound represented by following formula (B) in the same layer in the point of the effect of the present invention, and in this case it is more preferred to use both the compounds by coemulsifying them. In particular, it is preferred to use these compounds in a light-sensitive silver halide emulsion layer by copolymerizing them with a yellow dye-forming coupler or a magenta dye-forming coupler.

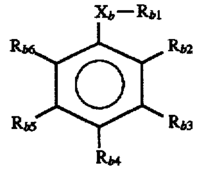
(B)

wherein $R_{b1}$ represents an aliphatic group or a heterocyclic group; $R_{b2}$, $R_{b3}$, $R_{b4}$, $R_{b5}$, and $R_{b6}$, which may be the same or different, each represents a hydrogen atom, an aliphatic group, an aliphatic acyl group, an arylacyl group, an aliphatic acylamino group, an arylacylamino group, an aliphatic oxycarbonyl group, an aryloxycarbonyl group, a halogen atom, an aliphatic sulfonyl group, an arylsulfonyl group, a carbamoyl group, a sulfamoyl group, or —$X_{b'}$—$R_{b1'}$; $X_b$ and $X_{b'}$ each represents —O—, —S—, or —N($R_{b7}$)—; $R_{b1'}$, and $R_{b7}$ each has the same meaning as $R_{b1}$; the substituents which are the ortho-positions with each other in —$X_b$—$X_{b1}$, $R_{b2}$ to $R_{b6}$ may combine with each other to form a 5- to 8-membered ring; $R_{b1}$ and $R_{b7}$ or $R_{b1'}$ and $R_{b7}$ may combine with each other to form a 5- to 7-membered ring; and at least one of $R_{b2}$ to $R_{b6}$ is —$X_{b'}$—$R_{b1'}$.

Then, the formula (B) is explained in detail.

In the formula (B), $R_{b1}$ represents an aliphatic group which may have a substituent (preferably, an alkyl group having from 1 to 30 carbon atoms which may have a substituent, e.g., methyl, i-propyl, benzyl, hexadecyl, cyclohexyl, 2-phenoxyethyl, and 2-methanesulfonamidoethyl) or a heterocyclic group which may have a substituent (preferably, a saturated heterocyclic group having from 3 to 30 carbon atoms, e.g., 2-tetrahydropyranyl).

$R_{b2}$, $R_{b3}$, $R_{b4}$, $R_{b5}$, and $R_{b6}$, which may be the same or different, each represents a hydrogen atom, an aliphatic group which may have a substituent (preferably, an alkyl group having from 1 to 30 carbon atoms which may have a substituent, e.g., methyl, t-octyl, benzyl, cyclohexyl, n-dodecyl, and s-butyl, 1,1-dimethyl-4-methoxycarbonylbutyl), an aliphatic acyl or arylacyl group which may have a substituent (preferably, an alkylacyl group having from 2 to 36 carbon atoms which may have a substituent or an arylacyl group having from 7 to 43 carbon atoms which may have a substituent, e.g., acetyl, pivaloyl, dodecanoyl, benzoyl, and 3-hexadecyl oxybenzoyl), an aliphatic acylamino or arylacylamino group which may have a substituent (preferably, an alkylacylamino group having from 2 to 36 carbon atoms which may have a substituent or an arylacylamino group having from 7 to 43 carbon atoms which may have a substituent, e.g., acetamino, pivaloylamino, 2-ethylhexanoylamino, 2-(2,4-di-t-amylphenoxy)octanoylamino, dodecanoylamino, and 3-butoxybenzoylamino), an aliphatic oxycarbonyl or aryloxycarbonyl group which may have a substituent (preferably, an alkoxycarbonyl group having from 2 to 36 carbon atoms which may have a substituent or an aryloxycarbonyl group having from 7 to 42 carbon atoms which may have a substituent, e.g., methoxycarbonyl, dodecyloxycarbonyl, 2-hexyloxyethoxycarbonyl, 2,4-di-t-amylphenoxycarbonyl, and 4-methoxyphenoxycarbonyl), a halogen atom (e.g., fluorine, chlorine, and bromine), an aliphatic sulfonyl or arylsulfonyl group which may have a substituent (preferably, having from 1 to 30 carbon atoms, e.g., methanesulfonyl, octanesulfonyl, 4-(4-t-octylphenoxy)butanesulfonyl, and 4-dodecyloxybenzenesulfonyl), a carbamoyl group which may have a substituent (preferably, a carbamoyl group having from 2 to 36 carbon atoms which may have a substituent, e.g., methylcarbamoyl, diethylcarbamoyl, and N-methyl-N-phenylcarbamoyl), a sulfamoyl group which may have a substituent (preferably, a sulfamoyl group having from 1 to 30 carbon atoms which may have a substituent, e.g., methylsulfamoyl, dibutylsulfamoyl, and phenylsulfamoyl), or —$X_{b'}$—$R_{b1'}$.

$X_b$ and $X_{b'}$ each represents —O—, —S—, or —N($R_{b7}$). Also, the substituents which are at the ortho-positions with each other in —$X_b$—$R_{b1}$, $R_2$ to $R_{b6}$ may combine with each other to form a 5- to 8-membered ring (e.g., a coumaran ring, a chroman King, an indan ring, and a quinoline ring each may have a substituent, and these rings each may further form a spiro ring or a bicyclo ring.

Furthermore, $R_{b1}$ and $R_{b7}$, or $R_{b1'}$ and $R_{b7}$ may combine with each other to form a 5- to 7-membered ring (e.g., a piperzine ring and a morpholine ring each may have a substituent); $R_{b1'}$ and $R_{b7}$ have the same meaning as $R_{b1}$, and at least one of $R_{b2}$ to $R_{b6}$ is —$X_{b'}$—$R_{b1'}$.

From the point of the effect of the present invention, $R_{b1}$, $R_{b1'}$, and $R_{b7}$ are preferably an alkyl group and $R_{b2}$ to $R_{b6}$ each is preferably a hydrogen atom, an alkyl group, an acylamino group, or —$X_{b'}$—$R_{b1'}$.

From the point of the effect of the present invention, the compounds shown by following formulae (B - I) to (B - X) are more preferred.

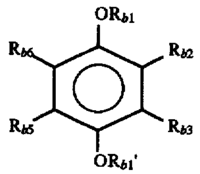

(B-I)

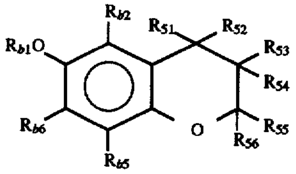

(B-II)

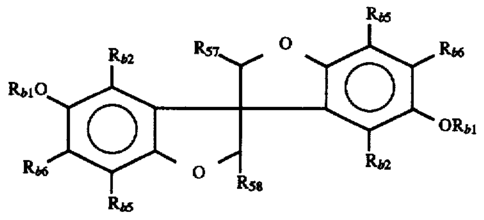

(B-III)

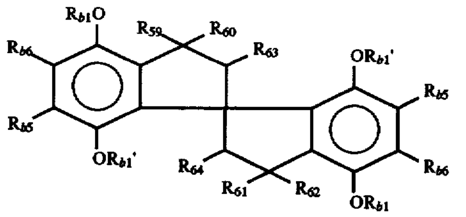

(B-IV)

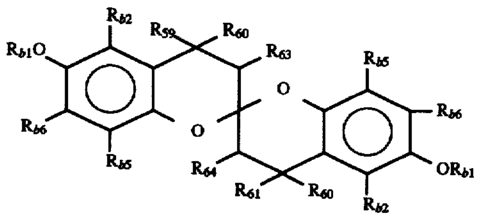

(B-V)

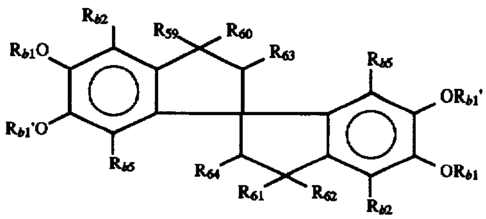

(B-VI)

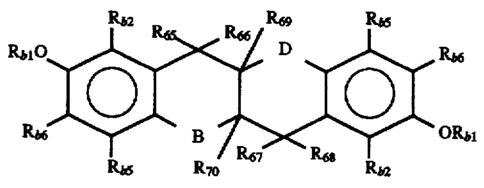

(B-VII)

-continued

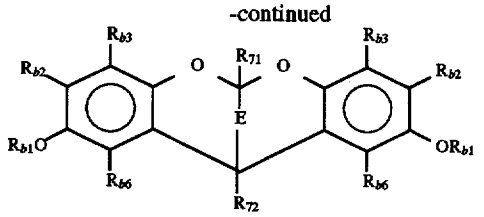

(B-VIII)

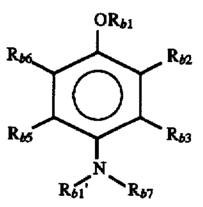

(B-IX)

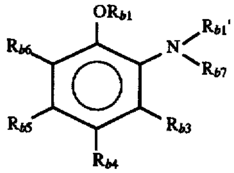

(B-X)

In the above formulae (B - I) to (B - X), $R_{b1}$ to $R_{b7}$ and $R_{b1'}$ have the same meaning as defined above for the formula (B).

$R_{51}$ to $R_{72}$, which may be the same or different, each represents a hydrogen atom, an alkyl group which may have a substituent (preferably, an alkyl group having from 1 to 20 carbon atoms which may have a substituent, e.g., methyl, ethyl, i-propyl, octadecyl, and benzyl), or an aryl group which may have a substituent .(preferably, a phenyl group having from 6 to 26 carbon atoms which may have a substituent, e.g., phenyl and 4-methylphenyl).

$R_{54}$ and $R_{55}$, or $R_{55}$ and $R_{56}$ may combine with each other to form a 5- to 7-membered hydrocarbon ring.

B and D each represents a single bond, —$C(R_{80})(R_{81})$— or —O— and E represents a single bond or —$C(R_{80})(R_{81})$— [wherein $R_{80}$ and $R_{81}$, which may be the same or different, each represents a hydrogen atom, an alkyl group (preferably, an alkyl group having from 1 to 20 carbon atoms which may have a substituent, e.g., methyl, ethyl, i-propyl, dodecyl, and benzyl), or an aryl group (preferably, a phenyl group having from 6 to 26 carbon atoms which may have a substituent, e.g., phenyl and 4-methylphenyl).

In the compounds shown by the formulae (B - I) to (B - X) described above, the compounds shown by the formulae (B - I), (B - III), (B - IV), (S - V), (S - VI), (B - VII), and (B - VIII) are preferred, the compounds shown by the formulae (B - IV), (B - VI), (B - VII), and (B - VIII) are more preferred, and the compounds shown by the formulae (B - IV) and (B - VI) are most preferred in the point of the effect of the present invention.

Then, specific examples of the compounds shown by the formula (B) are shown below but the compounds being used in the present invention are not limited to these compounds.

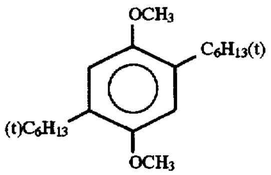
(B-1)
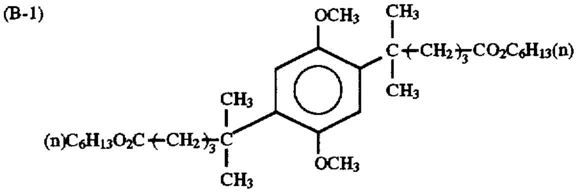
(B-2)
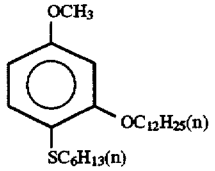
(B-3)
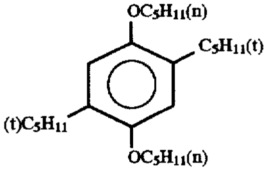
(B-4)
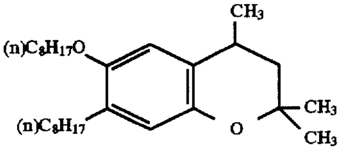
(B-5)
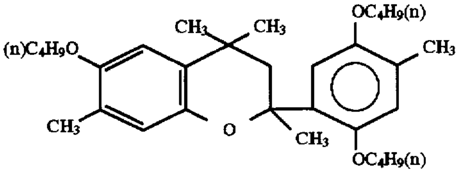
(B-6)
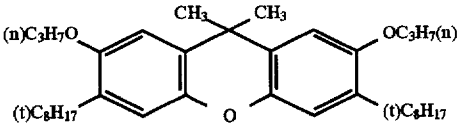
(B-7)
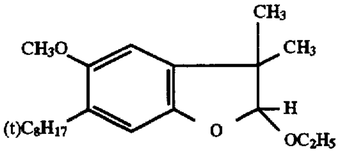
(B-8)
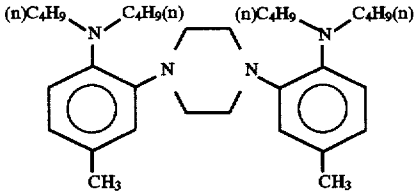
(B-9)
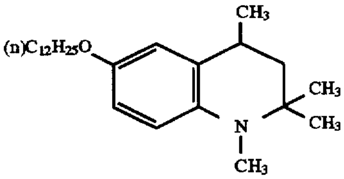
(B-10)
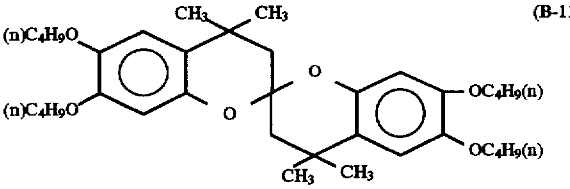
(B-11)
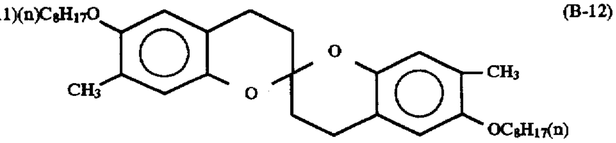
(B-12)
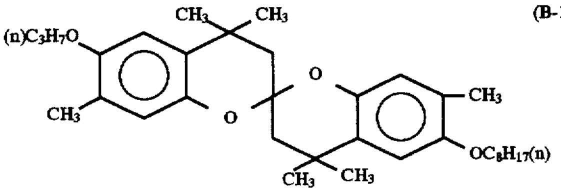
(B-13)
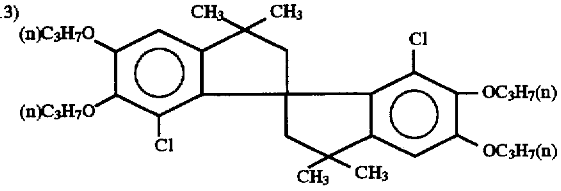
(B-14)
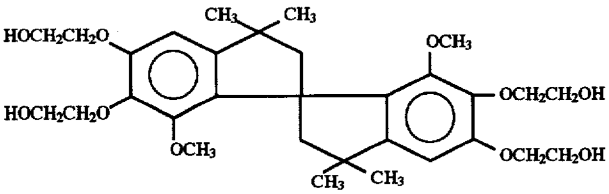
(B-15)

-continued
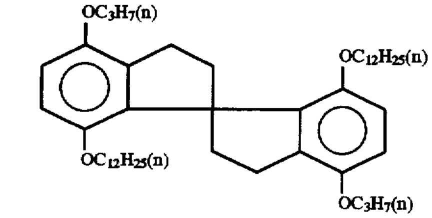
(B-16)
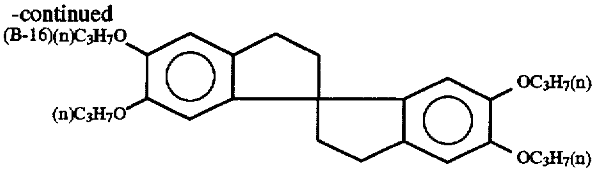
(B-17)
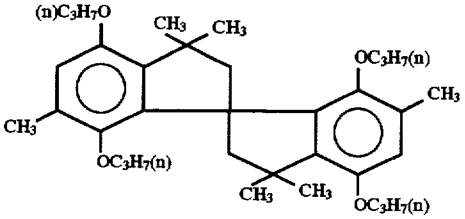
(B-18)
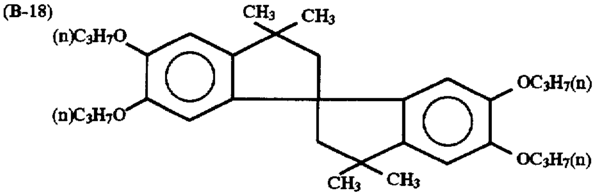
(B-19)
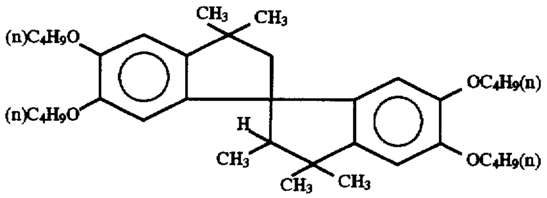
(B-20)
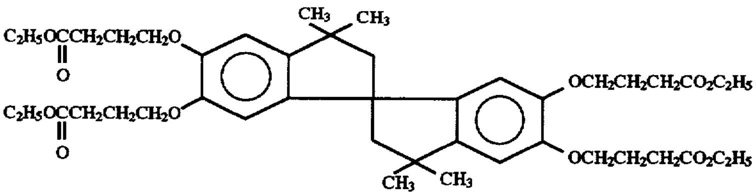
(B-21)
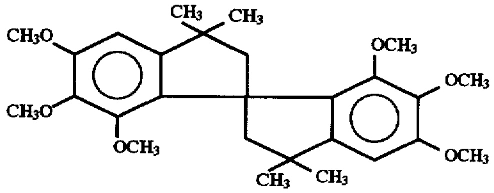
(B-22)
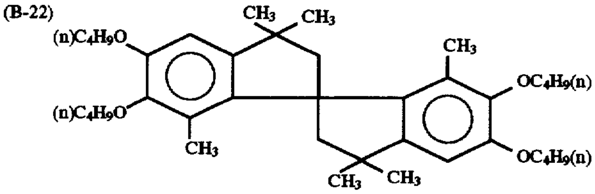
(B-23)
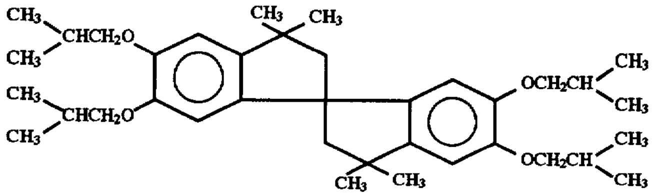
(B-24)
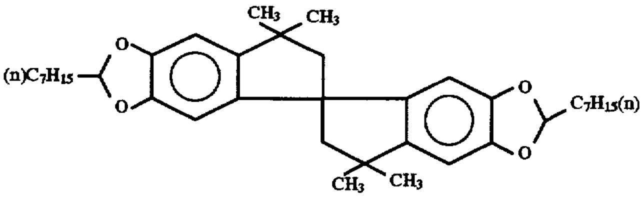
(B-25)
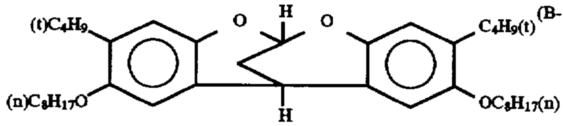
(B-26)
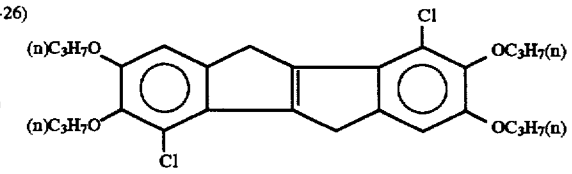
(B-27)

-continued
(B-28)
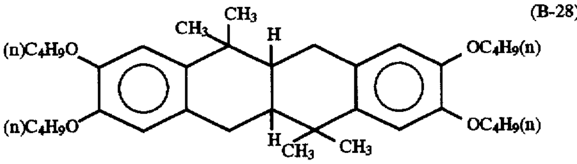
(B-29)
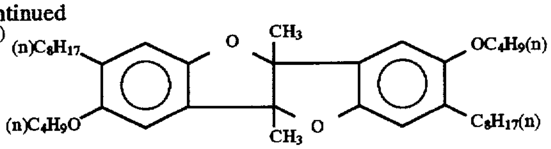
(B-30)
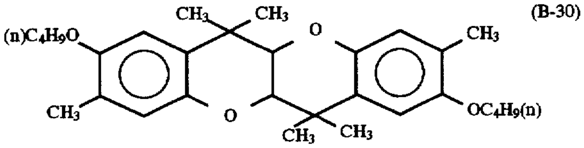
(B-31)
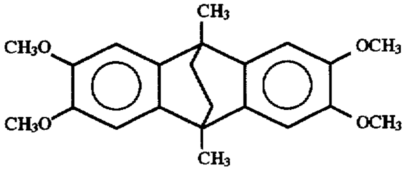
(B-32)
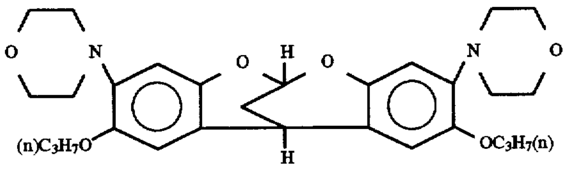
(B-33)
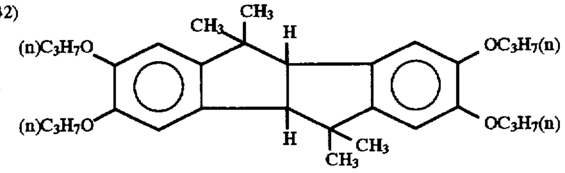
(B-34)
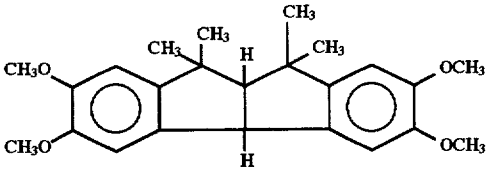
(B-35)
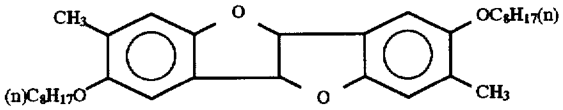
(B-36)
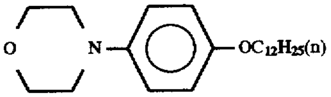
(B-37)
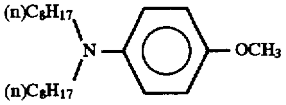
(B-38)
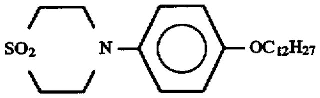
(B-39)
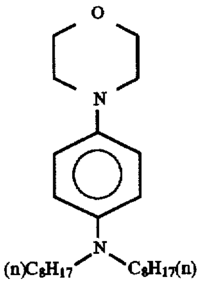
(B-40)
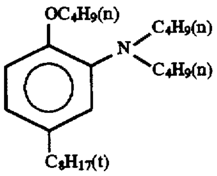
(B-41)
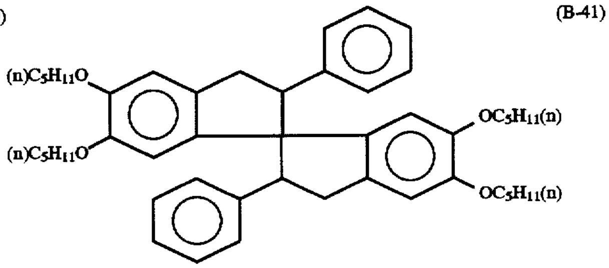
(B-42)
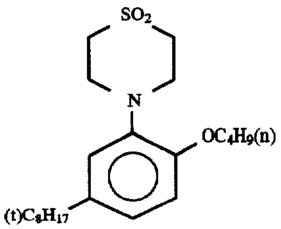
(B-43)
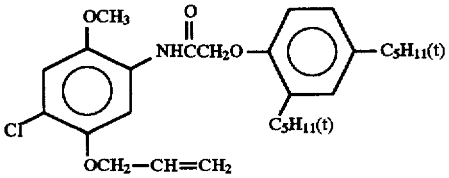

-continued

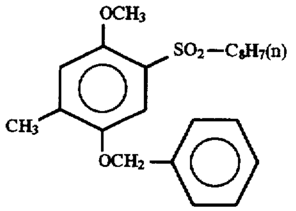

(B-44)

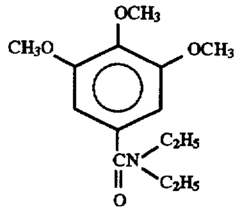

(B-45)

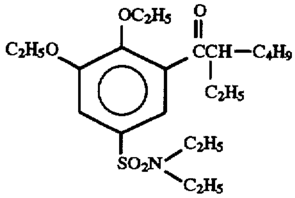

(B-46)

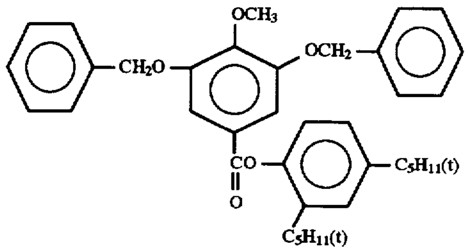

(B-47)

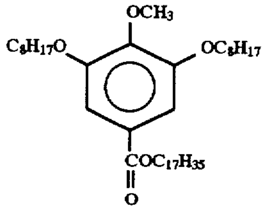

(B-48)

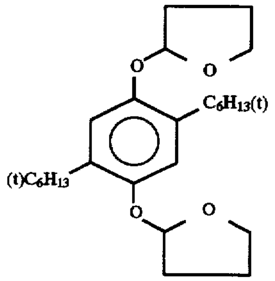

(B-49)

These compounds can be synthesized by the methods described in JP-B-45-14034, JP-B-56-24257, and JP-B-59-52421 (the term "JP-B" as used herein means an "examined published Japanese patent application"), JP-A-55-89835, JP-A-56-159644, JP-A-62-244045, JP-A-62-244246, JP-A-62-273531, JP-A-63-95439, JP-A-63-95448, JP-A-63-95450, JP-A-4-330440, and JP-A-58-105147, European Patent 239,972, etc., and the methods similar to the above methods.

In the present invention, the using amount of the compound shown by the formula (B) differs according to the kind and the amount of a coupler but is usually in the range of from 0.5 to 300 mole %, preferably from 1 to 200 mole %, and most preferably from 2 to 100 mole % per mole of the coupler being used in the same layer containing the compound (B).

The mole ratio of the compound shown by formula (A) to the compound shown by formula (B) in the same layer is preferably from 0.01 to 10.

The compounds shown by the formula (A) and the formula (B) being used in the present invention are the compounds for inhibiting fading of dye images formed from couplers and are non-coloring compounds- The non-coloring compound is a compound giving substantially no dye in the case of being processing with a color developer.

The compound shown by the formula (A) and the compound shown by the formula (B) being used in the present invention, and couplers can be introduced in the color photographic light-sensitive material of the present invention by various known dispersion methods and in this case, an oil-in-water dispersion method that these compounds are dissolved in a high-boiling organic solvent (if necessary, using a low-boiling organic solvent), the solution is dispersed by emulsification in an aqueous gelatin solution, and the emulsified dispersion is added to a silver halide emulsion is preferably used.

Examples of the high-boiling organic solvent being used for the oil-in-water dispersion method are described in U.S. Pat. No. 2,322,027, etc.

Also, practical examples of the step and the effect of a latex dispersion method as one of polymer dispersion methods and the latex for the impregnation are described in U.S. Pat. No. 4,199,363, West German Patent Applications (OLS) 2,541,274 and 2,541,230, JP-B-53-41091, European Patent 029,104A, etc., and also a dispersion method with an organic solvent-soluble polymer is described in PCT Patent Publication (unexamined) WO 88/00723.

As the high-boiling organic solvent which can be used for the oil-in-water dispersion method described above, there are phthalic acid esters [e.g., dibutyl phthalate, dioctyl phthalate, dicyclohexyl phthalate, di-2-ethylhexyl phthalate, dicyl phthalate, bis(2,4-di-tert-amylphenyl) isophthalate, and bis(1,1-diethylpropyl) phthalate], phosphoric acid or phosphonic acid esters (e.g., diphenyl phosphate, triphenyl phosphate, tricresyl phosphate, 2-ethylhexyldiphenyl phosphate, dioctyl butyl phosphate, tricyclohexyl phosphate, tri-2-ethylhexyl phosphate, tridecyl phosphate, and di-2-ethylhexylphenyl phosphate), benzoic acid esters (e.g., 2-ethylhexyl benzoate, 2,4-dichlorobenzoate, dodecyl benzoate, and 2-ethyl hexyl-p-hydroxy benzoate), amides (e.g, diethyldodecanamide), alcohols or phenols (e.g., isostearyl alcohol, laurylalcohol and 2,4-di-tert-amyl phenol), aliphatic esters (e.g., dibutoxyethyl succinate, di-2-ethylhexyl succinate, 2-hexyldecyl tetradecanate, and tributyl citrate), aniline derivatives (N,N-dibutyl-2-butoxy-5-tert-octylaniline, etc.), chlorinated paraffins (paraffins having a chlorine content of from 10% to 80%), trimesic acid esters (e.g., trimesic acid tributyl), dodecylbenzene, diisopropylnaphthalene, phenols [e.g., 2,4-di-tert-amylphenol, 4-dodecyloxyphenol, 4-dodecyloxycarbonylphenol, and 4-(4-dodecyloxyphenylsulfonyl)phenol], carboxylic acids [e.g., 2-(2,4-di-tert-amylphenoxybutyric acid, 2-ethoxyoctandecanic acid), and alkylphosphoric acids [e.g., di-2(ethylhexyl)phosphoric acid and disphenylphosphoric acid], etc.

Also, as an auxiliary solvent, an organic solvent having a boiling point of from 30° C. to about 160° C. (e.g., ethyl acetate, butyl acetate, ethyl propionate, methyl ethyl ketone, cyclohexanone, 2-ethoxyethl acetate, and dimethylformamide) may be used together with the high-boiling organic solvent.

The high-boiling organic solvent can be used in an amount of from 0 to 10.0 times, preferably from 0 to 5-0 times, and more preferably from 0 to 1.0 times by weight ratio to the coupler.

For preparing the silver halide color photographic material of the present invention, it is preferred to use a combination of a yellow dye-forming coupler, a magenta dye-forming coupler, and a cyan dye-forming coupler each coloring yellow, magenta, and cyan, respectively, by causing coupling with the oxidation product of an aromatic primary amino color developing agent.

The couplers being used as a combination thereof may be four-equivalent or two-equivalent to a silver ion, or may be polymers or oligomer forms. Furthermore, each of the couplers being used as the combination thereof may be single or a mixture of two or more kinds.

Then, couplers which cab be preferably used in the present invention are explained.

As the cyan dye-forming coupler, there are phenolic couplers and naphtholic couplers and the couplers described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Patent Publication (OLS) 3,329,729, European Patent Nos. 121,365A, 249,453A, and 333,185A2, U.S. Pat. Nos. 3,446,622, 4,333,999, 4,775,616, 4,451,559, 4,427,767, 4,690,889, 4,254,212, and 4,296,199, JP-A-61-42653 are preferable. Furthermore, the azole series couplers described in JP-A-64-553, JP-A-64-554, JP-A-64-555, and JP-A-64-556, European Patent Publications (unexamined) 488,248, 491,197, 484,909, 456,226, etc.; the imidazole series couplers described U.S. Pat. No. 4,818,672 and JP-A-2-33144; and the cyclic active methylene type cyan couplers described in JP-A-64-32260 can be used in this invention.

As the particularly preferred cyan dye-forming couplers, there are the couplers of the formulae (C - I) and (C - II) described in JP-A-2-139544 and the cyan couplers described in European Patent Publications (unexamined) 488,248, 491,197, 484,909, and 46,226.

As the magenta dye-forming coupler, 5-pyrazolone series couplers and pyrazoloazole series couplers are preferred, and the cyan couplers described in U.S. Pat. Nos. 4,310,619 and 4,351,897, European Patent 73,636, U.S. Pat. Nos. 3,061,432 and 3,725,067, *Research Disclosure*, No. 24220 (June, 1984), ibid., No. 24230 (June, 1984), JP-A-60-33552, JP-A-60-43659, JP-A-61-72238, JP-A-60-35730, JP-A-55-118034, JP-A-60-185951, U.S. Pat. Nos. 4,500,630, 4,540,654, and 4,556,639, and PCT Patent Publication (unexamined) WO 88/04795 are more preferable.

As the particularly preferred magenta dye-forming coupler. there are the pyrazoloazole series magenta dye-forming couplers shown by the formula (I) described in JP-A-2-139544 and the 5-pyrazolone series magenta dye-forming couplers shown by the formula (M - 1) described in JP-A-2-139544. The most preferred magenta dye-forming couples are the pyrazoloazole series magenta dye-forming couplers described above.

As the yellow dye-forming coupler, the couplers described in U.S. Pat. Nos. 3,933,501, 4,022,620, 4,326,024, 4,401,752, 4,248,961, 5,118,599, 3,973,968, 4,314,023, 4,511,649, and 5,118,599, European Patent 249,473A, JP-A-63-23145, JP-A-63-123047, JP-A-1-250944, JP-A-1-213648, JP-B-58-10739, British Patents 1,425,020 and 1,476,760 can be used without giving bad influences on the effect of the present invention.

The compound shown by the formula (A) described above being used in the present invention is particularly preferred in the case of being used by coemulsifying with a yellow dye-forming coupler in the point of the effect of this invention and in this case, the yellow dye-forming couplers shown by the following formula (Y) are preferably used.

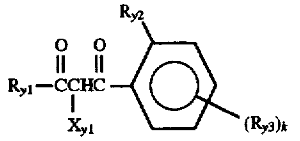

(Y)

wherein $R_{y1}$ represents an alkyl group, a substituted amino group, or a heterocyclic group; $R_{y2}$ represents a halogen atom, an alkoxy group, or an aryloxy group; $R_{y3}$ represents a group which can be substituted with a benzene ring; $X_{y1}$ represents a hydrogen atom or a group capable of splitting off upon coupling reaction with the oxidation product of an aromatic primary amine developing agent (hereinafter referred to as a splitting group) by the coupling reaction with the oxidation product of an aromatic primary amino color developing agent; k represents an integer of from 0 to 4, and when k is 2 or more, plural $R_{y3}$'s may be the same or different.

$R_{y1}$ preferably represents an alkyl group having from 1 to 20 carbon atoms (e.g., methyl, ethyl, t-butyl, 1-methylcyclopropyl, 1-ethylcyclopropyl, 1-benzylcyclopropyl, adamantyl and tetradecyl), a substituted amino group having from 1 to 36 carbon atoms (e.g., dimethylamino, dibutylamino, N-methyl-N-phenylamino and phenylamino), or a heterocyclic group having from 1 to 36 carbon atoms (e.g., 4,4-dimethyl-3,5-dioxacyclohexyl, indolinyl, pyperidine-1-yl and morpholine-1-yl).

$R_{y2}$ preferably represents a halogen atom (e.g., fluorine, chlorine and bromide), an alkoxy group having from 1 to 20 carbon atoms (e.g., metholy, ethoxy, benzyloxy, cyclohexyloxy and octyloxy), or an aryloxy group having from 1 to 36 carbon atoms (e.g., phenoxy, p-methylphenoxy and m-chlorphenoxy).

Preferred examples of $R_3$ include the embodiment set forth above as preferred examples for $R_{a2}$.

As the particularly preferred yellow dye-forming couplers, there are the yellow dye-forming couplers shown in the above formula (Y) described in JP-A-2-139544, and acylacetamide series yellow dye-forming couplers having a feature in the acryl group described in JP-A-5-2248 and European Patent Publication (unexamined) 0447,969, and the yellow dye-forming couplers shown by the formula (Cp - 2) described in European Patent Publication (unexamined) 0446863A2.

When the compound shown by the formula (A) is used by coemulsifying with the yellow dye-forming coupler, it is also preferred that they are used by coemulsifying with the polymer of acrylic acid amide or methacrylic acid amide as a monomer.

A coupler releasing a photographically useful residue with coupling can be also used in the present invention. As the DIR coupler releasing a development inhibitor, the couplers described in the patents described in *Research Disclosure*, No. 17643, Paragraphs VII to F, JP-A-57-151944, JP-A-57-154234, JP-A-60-184248, JP-A-63-37346, U.S. Pat. Nos. 4,248,962 and 4,782,012 are preferred.

As the coupler imagewise releasing a nucleating agent or a development accelerator at development, the couplers described in British Patents 2,097,140 and 2,131,188, JP-A-59-157638, and JP-A-59-170840 are preferred.

As other couplers which can be used for the color photographic materials of the present invention, there are the competing couplers described in U.S.. Pat. No. 4,130,427; the multi-equivalent couples described in U.S. Pat. Nos. 4,283,472, 4,338,393, 4,310,618, etc.; the DIR redox compound-releasing couplers, the DIR coupler-releasing couplers, the DIR coupler-releasing redox compounds, and the DIR redox-releasing redox compounds described in JP-A-60-185950, JP-A-62-24252, etc.; the couplers releasing a dye which is recolored after being released described in European Patent 173,302A; the bleaching agent-releasing couplers described in *Research Disclosure*, No. 11449, ibid., No. 24241, JP-A-61-201247, etc.; the ligand-releasing couplers described in U.S. Pat. No. 4,553,477; the couplers releasing a leuco dye described in JP-A-63-75747, the couplers releasing a fluorescent dye described in U.S. Pat. No. 4,774,181, etc.

Then, typical examples of the couplers which can be used in the present invention are shown below.

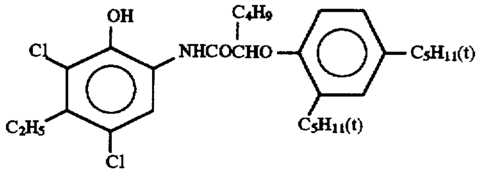

(C-1)

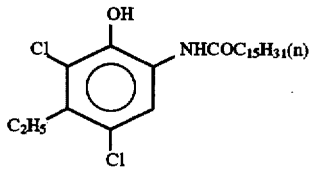

(C-2)

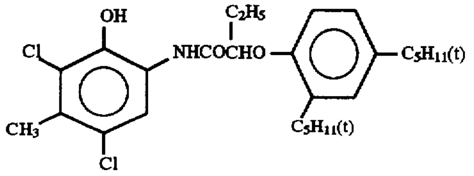

(C-3)

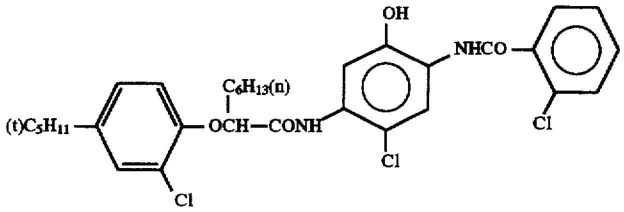

(C-4)

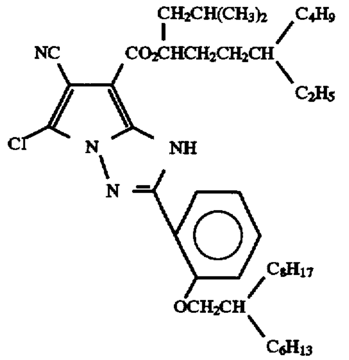

(C-5)

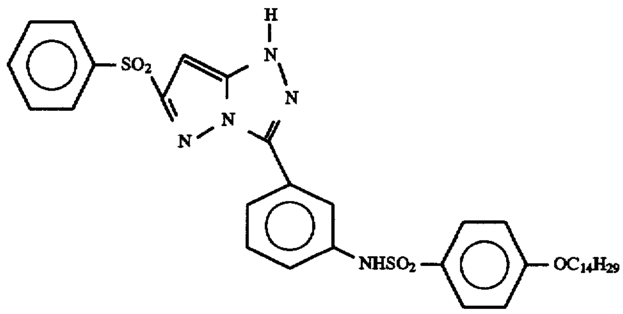

(C-6)

-continued
(C-7)
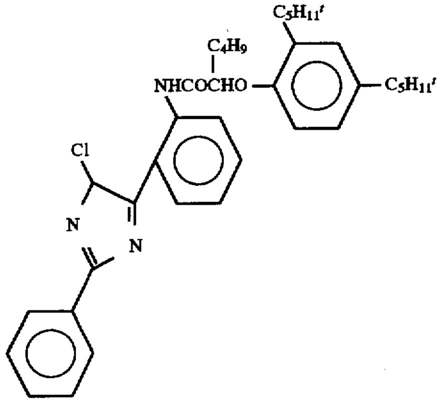
(C-8)
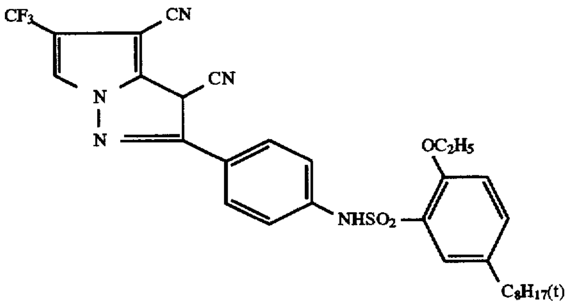
(C-9)
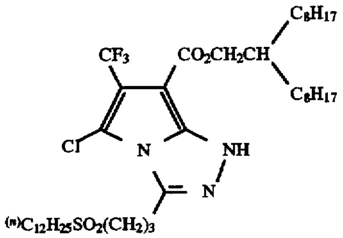
(C-10)
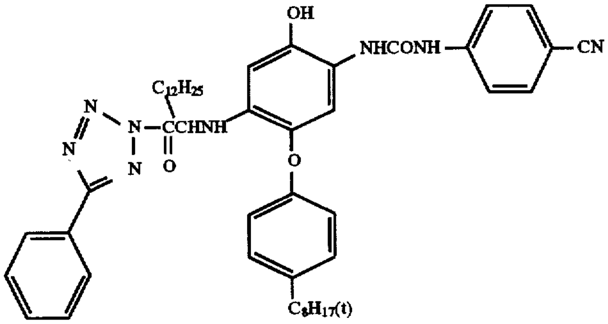
(C-11)
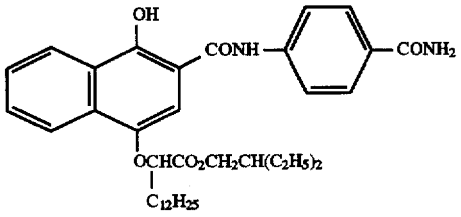
(C-12)
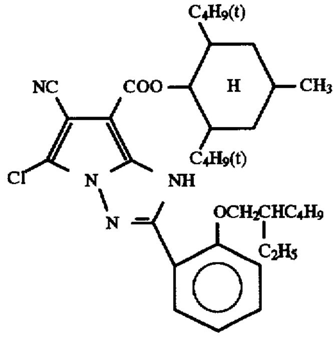

-continued
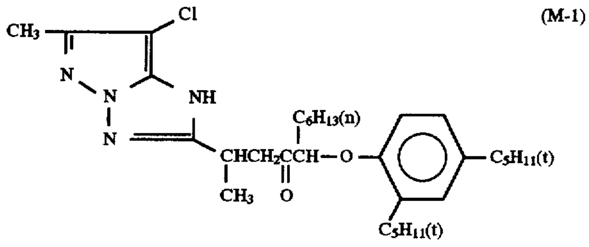
(M-1)
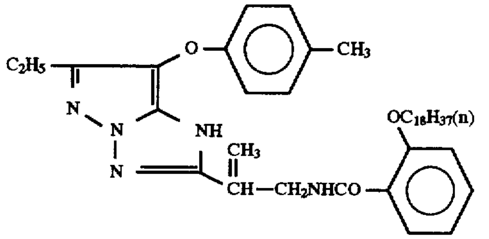
(M-2)
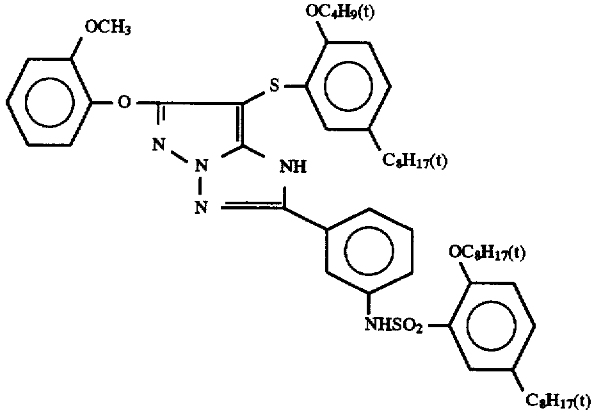
(M-3)
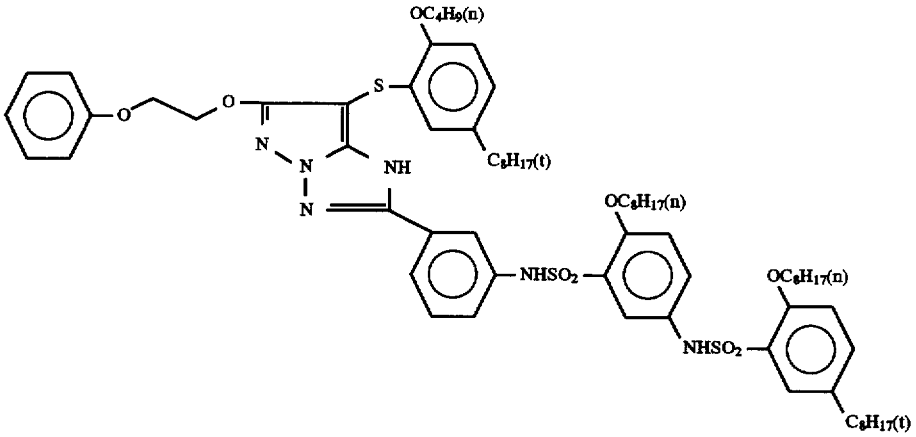
(M-4)
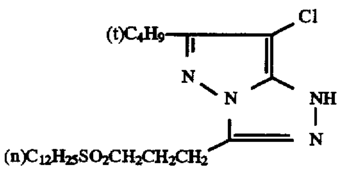
(M-5)
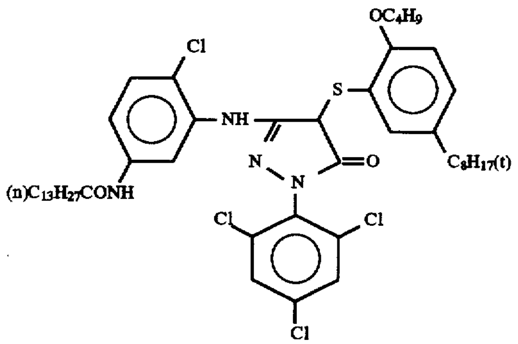
(M-6)

-continued
(M-7)
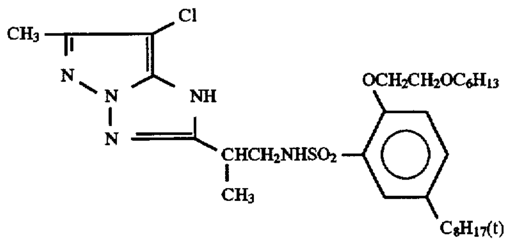
(M-8)
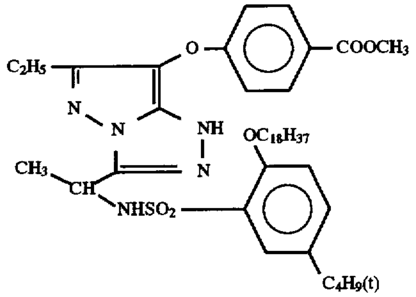
(M-9)
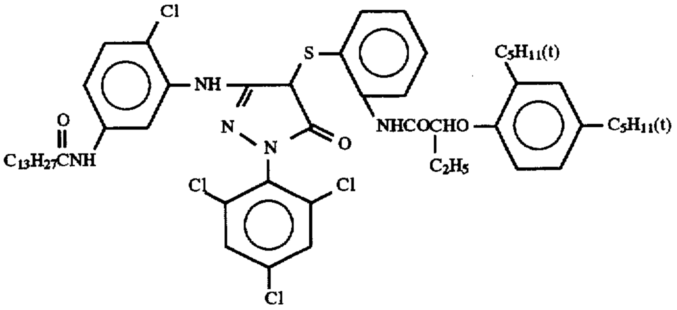
(M-10)
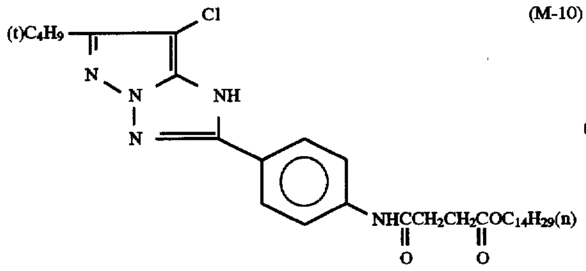
(Y-1)
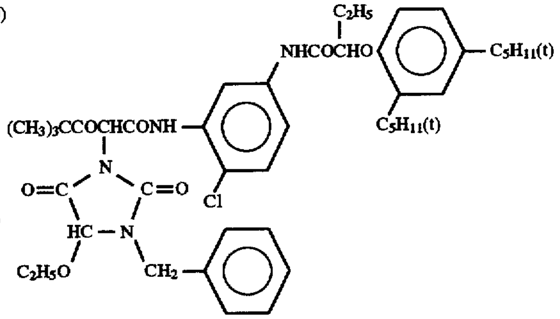
(Y-2)
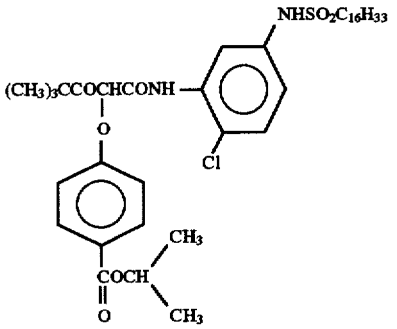
(Y-3)
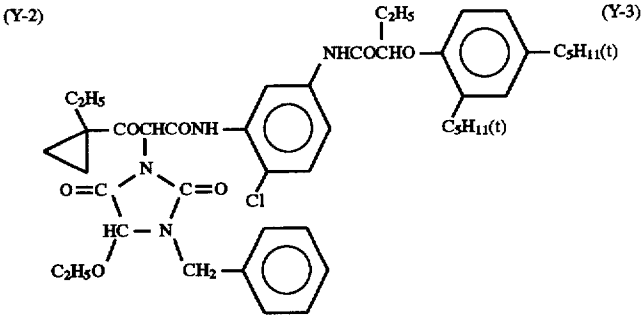
(Y-4)
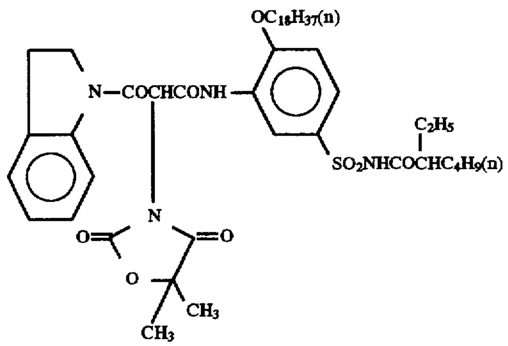

-continued

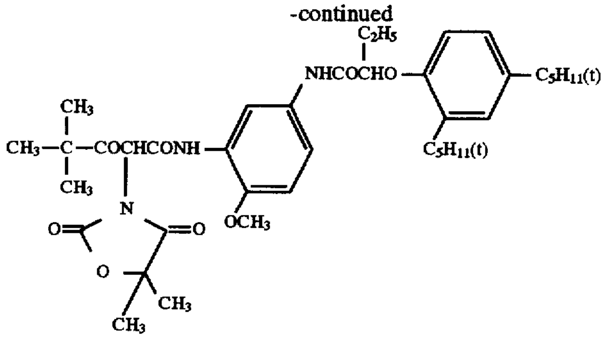

(Y-5)

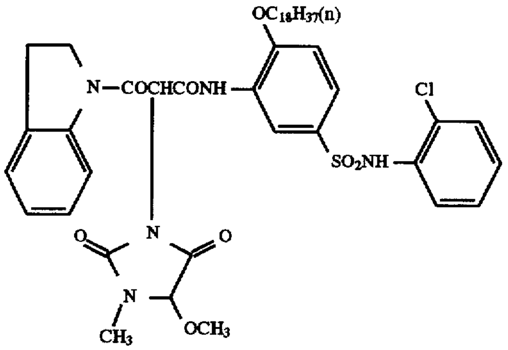

(Y-6)

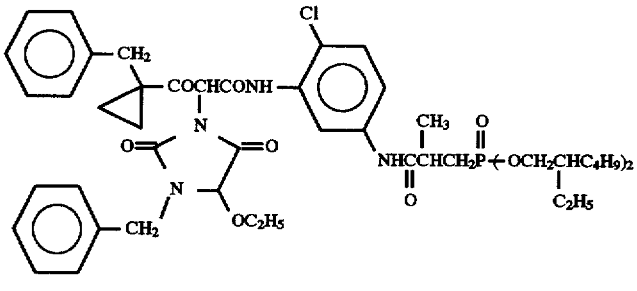

(Y-7)

The standard using amount of the coupler which can be used together with the compound of the formula (A) being used in the present invention is in the range of from 0.001 to 1 mole per mole of the light-sensitive silver halide in the same emulsion layer and is preferably in the range of from 0.01 to 0.5 mole for the yellow dye-forming coupler, from 0.003 to 0.3 mole for the magenta dye-forming coupler, and from 0.002 to 0.3 mole for the cyan dye-forming coupler.

For the color photographic material of the present invention, various known fading inhibitors can be used together.

As typical examples of organic fading inhibitors for the cyan, magenta and/or yellow images, there are hydroquinones, 6-hydroxychromans, 5-hydroxycoumarans, spirochromans, p-alkoxyphenols, hindered phenols such as bisphenols, gallic acid derivatives, methylenedioxybenzenes, aminophenols, hindered amines, and the ether or ester derivatives obtained by silylating or alkylating the phenolic hydroxy group of each of these compounds.

Also, metal complexes such as (bissalitylaldoxymate) nickel complex and (bis-N,N-dialkyldithiocarbamate) nickel complex can be used.

As practical examples of the organic fading inhibitors, there are hydroquinones described in U.S. Pat. Nos. 2,360, 290, 2,418,613, 2,700,453, 2,701,197, 2,728,659, 2,730,300, 2,735,765, 3,982,944, and 4,430,425, British Patent 1,363, 921, U.S. Pat. Nos. 2,710,801, 2,816,028, etc.; the 6-hydroxychromans, 5-hydroxycoumarans, and spirochrmans described in U.S. Pat. Nos. 3,432,300, 3,573,050, 3,574,627, 3,698,909, and 3,764,337, JP-A-52-15225, etc., the p-alkoxyphenols described in U.S. Pat. No. 2,735,765, British Patent 2,066,975, JP-A-59-10539, JP-B-57-19765, etc.; the hindered phenols described in U.S. Pat. Nos. 3,700,455 and 4,228,235, JP-A-52-72224, JP-B-52-6623, etc.; the gallic acid derivatives described in U.S. Pat. Nos. 3,457,079; the methylenedioxybenzenes described in U.S. Pat. No. 4,332,886; the aminophenols described in JP-B-56-21144; the hindered amines described in U.S. Pat. Nos. 3,336,135 and 4,268,593, British Patents 1,326,889, 1,354, 313, and 1,410,846, JP-B-51-1420, JP-A-58-114036, JP-A-59-53846, JP-A-59-78344, etc.; and the metal complexes described in U.S. Pat. Nos. 4,050,938 and 4,241,155, British Patent 2,027,731A, etc.

By coemulsifying the foregoing compound with the coupler in an amount of usually from 5 to 100% by weight to the coupler and adding to the light-sensitive emulsion layer, the purpose thereof can be attained.

In the case of using the compound shown by the formula (A) being used in the present invention in the same emulsion layer with a yellow dye-forming coupler, it is also preferred to use the amide polymer of acrylic acid amide or methacrylic acid amide as the monomer together since the fading inhibiting effect is improved.

The color photographic light-sensitive material of this invention may contain a hydroquinone derivative, an aminophenol derivative, a gallic acid derivative, an ascorbic acid derivative, etc., as a color fog inhibitor. Also, for inhibiting the deterioration of cyan dye images by heat and, in particular,.light, it is effective to introduce a ultraviolet absorbent to the layers adjusting to both sides of a cyan coloring emulsion layer. Also such a ultraviolet absorbent may be incorporated in the layer farthest from the support, the layer containing a yellow dye-forming coupler, or an interlayer.

As the ultraviolet absorbent, there are the aryl group-substituted benzotriazole compounds described in U.S. Pat. No. 3,533,794; the 4-thiazolidone compounds described in U.S. Pat. Nos. 3,314,794 and 3,352,681; the benzophenone compounds described in JP-A-46-2748 and European Patent Publication (unexamined) 521,823, the cinnamic acid ester compounds described in U.S. Pat. Nos. 3,705,805 and 3,707,395; the butadiene compounds described in U.S. Pat. No. 4,045,229; the triazine compounds described in JP-A-46-3335 and European Patent Publication (unexamined) 520,938; and the benzoxazole compounds described in U.S. Pat. Nos. 3,406,070 and 4,271,307.

Furthermore, ultraviolet absorbing couplers (e.g., α-naphthol series cyan dye-forming couplers) or ultraviolet absorbing polymers may be used.

These ultraviolet absorbent may be mordanted to a specific layer. In the above-described compounds, the aryl group-substituted benzotriazole compounds and triazine compounds are preferred.

Also, it is preferred that for the color photographic light-sensitive material of this invention, the dye image storage- stability improving compounds as described in European Patent Publication (unexamined) 277,589A2 is used together with the coupler. In particular, it is preferred to use the foregoing compound together with an azole-series magenta dye-forming coupler or cyan dye-forming coupler. That is, it is preferred to use the compound (A) of forming a chemically inactive and substantially colorless compound by chemically bonding to an aromatic amino color developing agent remaining after color development described in European Patent Publication (unexamined) 277,589A2 and/or the compound (B) of forming a chemically inactive and substantially colorless compound by chemically bonding to the oxidation product of an aromatic amino color developing agent remaining after color development described in European Patent Publication (unexamined) 277,589A2 simultaneously or singly for inhibiting the formation of stains and other side-actions by the reaction of the couplers with the color developing agent or the oxidation product thereof remaining in the photographic layers during storage of the color images after processing.

Also, it is preferred to add the antifungal agent as described in JP-A-63-271247 to the color photographing light-sensitive material of the present invention for inhibiting the growth of various bacteria and fungi which grow in the hydrophilic colloid layers to deteriorate the color images.

As the silver halide being used in the present invention, silver chloride, silver bromide, silver chlorobromide, silver iodochlorobromide, silver iodobromide, etc., can be used but in particular, for the purpose of quick processing, it is preferred to use silver chlorobromide containing substantially no silver iodide and having a silver chloride content of a least 90 mole %, preferably at least 95 mole %, and more preferably at least 98 mole % or to use pure silver chloride.

Also, for the purpose of improving the sharpness, etc., of the color images, it is preferred that the color photographic light-sensitive material of the present invention contains the dyes (in particular, oxonol series dyes) capable of being discolored by processing described in European Patent Publication (unexamined) 337,490A3, pages 27 to 76 in the hydrophilic colloid layer such that the optical reflection density of the color photographic light-sensitive material at 680 nm becomes at least 0.70 and also contains at least 12% by weight (more preferably at least 14% by weight) of titanium oxide surface treated with a dihydric to tetrahydric alcohol (e.g., trimethylolethane) in the water resisting resin layer of the support.

Furthermore, as the support being used for the color photographic light-sensitive material of this invention, a white polyester series support or a support having formed on the support at the side of forming the silver halide emulsion layer a layer containing a white pigment may be used for display.

Moreover, for improving the sharpness, it is preferred to form an antihalation layer on the support at the silver halide emulsion side or the back side.

In particular, in order that the color images of the color photographic material of this invention can be observed both a reflected light and a transmitted light, it is preferred that the transmission density of the support is selected in the range of from 0.35 to 0.8.

The color photographic light-sensitive material of the present invention may be exposed with a visible light or an infrared light. As the exposing method, a low-illumination exposure or a high-illumination short-time exposure may be employed. In particular, in the latter case, a laser scanning exposure system that the exposure time per one pixcel is shorter than $10^{-4}$ second is preferred.

Also, at the exposure, the band and the stop filter described in U.S. Pat. No. 4,880,726 are preferably used, whereby light stain is removed and the color reproducibility is greatly improved.

The present invention is preferably applied to a color photographic light-sensitive material wherein a color developing agent (a para-phenylenediamine derivative) does not exist in the light-sensitive material before development processing, and can be applied to, for example, color photographic papers, color photographic reversal papers, direct positive color photographic light-sensitive materials, color photographic negative films, color photographic positive films, color photographic reversal films, etc. In these photographic materials, the present invention is preferably applied to color photographic light-sensitive materials having a reflective support (e.g., color photographic papers and color photographic reversal papers) and color photographic light-sensitive materials forming positive color images (e.g., direct positive color photographic light-sensitive materials, color positive photographic films, and color photographic reversal films) and in particular, the present invention is preferably applied to color photographic light-sensitive materials having a reflective support.

The color photographic light-sensitive material can be photographically processed by the ordinary methods described in *Research Disclosure*, No. 17643, pages 28 to 29 and ibid., No. 18716, page 615, the left column to the right column.

For example, a color development step, a desilvering step, and a washing step are carried out. In the desilvering step, in place of the bleaching step using a bleaching liquid and the fixing step using a fixing liquid, a bleach-fixing (blixing) step using a bleach-fixing (blixing liquid) can be employed, and also the beaching step, the fixing step, and the blixing step can be used in a desired combination. In place of the washing step, a stabilization step may be carried out and after the washing step, the stabilization step may be carried out. Also, a monobath processing step using a monobath developing, bleaching, fixing liquid which performs a color development, a bleach, and a fix in one bath. Also, by combining these processing steps, a pre-hardening processing step, the neutralization step, a stop fix processing step, a pose hardening processing step, a controlling step, an intensifying step, etc., may be carried out. Between the foregoing steps, an optional intermediate washing step may be employed. Also, in these processing steps, in place of the color development step, a so-called activator processing step may be employed.

The silver halide emulsions, other materials (additives, etc.), photograph constituting layers (layer displacement, etc.) being used for the color photographic light-sensitive materials of this invention, and the processing processes and additives for the processing liquids being applied for processing the color photographic light-sensitive materials of this invention are described in JP-A-4-359349 and the following patent publications, in particular, European Patent (unexamined) 355,660A2 (EP 355.660A2) as shown in Table 1 below.

TABLE 1

| Photographic Constitutional Element | JP-A-62-215272 | JP-A-2-33144 | EP 0,355,660A2 |
|---|---|---|---|
| Silver Halide Emulsion | p. 10, right upper column, l 6 to p. 12, left lower column, l. 5<br>p. 12, right lower column, 4 line up from the bottom to p. 13, left upper column, l. 17 | p. 28, right upper column, l. 16 to p. 29, right lower column, l. 11<br>p. 30, ll. 2 to 5 | p. 45, l 53 to p. 47, l. 3<br>p. 47, ll. 20 to 22 |
| Silver Halide Solvent | p. 12, left lower column, ll. 6 to 14<br>p. 13, left upper column, 3 line up from the bottom to p. 18, left lower column, last line | — | — |
| Chemical Sensitizer | p. 12, left lower column, 3 line up from the bottom to right lower column, 5 line up from the bottom<br>p. 18, right lower column, l. 1 to p. 22, right upper column, 9 line up from the bottom | p. 29, right lower column, l. 12 to last line | p. 47, ll. 4 to 9 |
| Spectral Sensitizer (spectral sensitizing method) | p. 22, right upper column, 8 line up from the bottom to p. 38, last line | p. 30, left upper column, ll. 1 to 13 | p. 47, ll. 10 to 15 |
| Emulsion Stabilizer | p. 39, left upper column, l. 1 to p. 72, right upper column, last line | p. 30, left upper column, l. 14 to right upper column, l. 1 | p. 47, ll. 10 to 15 |
| Development Accelerator | p. 72, left lower column, l. 1 to p. 91, right upper column, l. 3 | — | — |
| Color Coupler (cyan, magenta, yellow) | p. 91, right upper column, l. 4 to p. 121, left upper column, l. 6 | p. 3, right upper column, l. 14 to p. 18, left upper column, last line<br>p. 30, right upper column, l. 6 to p. 35, right lower column, l. 11 | p. 4, ll. 15 to 27<br>p. 5, l. 30 to p. 28, last line<br>p. 45, ll. 29 to 31<br>p. 47, l. 23 to p. 63 l. 50 |
| Supersensitizer | p. 121, left upper column, l. 7 to p. 125, right upper column, l. 1 | — | — |
| UV Absorbing Agent | p. 125, right upper column, l. 2 to p. 127, left lower column, last line | p. 37, right lower column, l. 14 to p. 38, left upper column, l. 11 | p. 65, pp. 22 to 31 |
| Discoloration Inhibitor (image stabilizing method) | p. 127, right lower column, l. 1 to p. 137, left lower column, l. 8 | p. 36, right upper column, l. 12 to p. 37, left upper column, l. 19 | p. 4, l. 30 to p. 5, l. 23<br>p. 29, l. 1 to p. 45, l. 25<br>p. 45, ll. 33 to 40<br>p. 65, ll. 2 to 21 |
| High Boiling Point and/or Low Boiling Point Organic Solvent | p. 137, left lower column, l. 9 to p. 144, right upper column, last line | p. 35, right lower column, l. 14 to p. 36, left upper column, 4 line up from the bottom | p. 64, ll. 1 to 51 |
| Dispersing Method of Photographic Additives | p. 144, left lower column, l. 1 to p. 146, right upper column, l. 7 | p. 27, right lower column, l. 10 to p. 28, left upper column, last line<br>p. 35, right lower column, l. 12 to p. 36, right upper column, l. 7 | p. 63, l. 51 to p. 64, l. 56 |
| Hardening Agent | p. 146, right upper column, l. 8 to p. 155, left lower | — | — |

TABLE 1-continued

| Photographic Constitutional Element | JP-A-62-215272 | JP-A-2-33144 | EP 0,355,660A2 |
|---|---|---|---|
| | column, l. 4 | | |
| Developing Agent Precursor | p. 155, left lower column, l. 5 to p. 155, right lower column, l. 2 | — | — |
| DIR Compound | p. 155, right lower column, ll. 3 to 9 | — | — |
| Support | p. 155, right lower column, l. 19 to p. 156, left upper column, l. 14 | p. 38, right upper column, l. 18, to p. 39, left upper column, l. 3 | p. 66, l. 29 to p. 67, l. 13 |
| Composition of Light-Sensitive Layer | p. 156, left upper column, l. 15 to p. 156, right lower column, l. 14 | p. 28, right upper column, ll. 1 to 15 | p. 45, ll. 41 to 52 |
| Dye | p. 156, right lower column, l. 15 to p. 184, right lower column, last line | p. 38, left upper column, l. 12 to right upper column, l. 7 | p. 66, ll. 18 to 22 |
| Emulsion Stabilizer | p. 39, left upper column, l. 1 to p. 72, right upper column, last line | p. 30, left upper column, l. 14 to right upper column, l. 1 | p. 47, ll. 10 to 15 |
| Color Mixture Inhibitor | p. 185, left upper column, l. 1 to p. 188, right lower column, l. 3 | p. 36, right upper column, ll. 8 to 11 | p. 64, l. 57 to p. 65, l. 1 |
| Gradation Controlling Agent | p. 188, right lower column, ll. 4 to 8 | — | — |
| Stain Inhibitor | p. 188, right lower column, l. 9 to p. 193, right lower column, l. 10 | p. 37, left upper column, last line to right lower column, l. 13 | p. 65, l. 32 to p. 66, l. 17 |
| Surfactant | p. 201, left lower column, l. 1 to p. 210, right upper column, last line | p. 18, right upper column, l. 1 to p. 24, right lower column, last line p. 27, left lower column, 10 line up from the bottom to right lower column, l. 9 | — |
| Fluorine-Containing Compound (as anti-static agent, coating aid, lubricant, adhesion preventive agent) | p. 210, left lower column, l. 1 to p. 222, left lower column, l. 5 | p. 25, left upper column, l. 1 to p. 27, right lower column, l. 9 | — |
| Binder (hydrophilic colloid) | p. 222, left lower column, l. 6 to p. 225, left upper column, last line | p. 38, right upper column, ll. 8 to 18 | p. 66, ll. 23 to 28 |
| Tackifier | p. 225, right upper column, l. 1 to p. 227, right upper column, l. 2 | — | — |
| Antistatic Agent | p. 227, right upper column, l. 3 to p. 230, left upper column, l. 1 | — | — |
| Polymer Latex | p. 230, left upper column, l. 2 to p. 239, last line | — | — |
| Matting Agent | p. 240, left upper column, l. 1 to p. 240, right upper column, last line | — | — |
| Photographic Processing Method (processing step or additives) | p. 3, right upper column, l. 7 to p. 10, right upper column, l. 5 | p. 39, left upper column, l. 4 to p. 42, left upper column, last line | p. 67, l. 14 to p. 69, l. 28 |

Note) References in column JP-A-62-215272 include contents amended by The Amendment dated March 16, 1987, which appears at the end of the Patent Publication.
Of couplers described above, so-called short wave type yellow couplers disclosed in JP-A-63-231451, JP-A-63-123047, JP-A-63-241547, JP-A-1-173499, JP-A-1-213648 and JP-A-1-250944 are preferably used as yellow couplers.

Then, the following examples are intended to illustrate the present invention but not to limit the invention in any way.

EXAMPLE 1

To 16.1 g of a yellow dye-forming coupler (Y - 1) was added 16.1 g of dibutyl phthalate as a high-boiling organic solvent and then 24 ml of ethyl acetate was added thereto to dissolve the coupler. The solution was dispersed by emulsification in 200 g of an aqueous solution of 10% by weight gelatin containing 1.5 g of sodium dodecylbenzenesulfonate.

The total amount of the emulsified dispersion was added to 247 g of a high silver chloride emulsion (silver 70.0 g/kg emulsion, silver bromide content 0.5 mole %), the emulsion obtained was coated on a triacetyl acetate film base having a subbing layer at a silver coverage of 1–73 g/$m^2$ and a gelatin layer was formed on the emulsion layer as a protective layer at a dry thickness of 1.0 μm to provide sample 101. In addition, as a gelatin hardening agent, 1-oxy-3,5-dichloro-s-triazine sodium salt was used.

By following the same procedure as the case of preparing sample 101 except that in the case of preparing the emulsified dispersion, each of the yellow couplers [the equivalent amount to the coupler (Y - 1)] shown in Table A below was coemulsified with each of the dye image stabilizers (A) [the compounds shown by the formula (A); the addition amount was shown in Table A] and the dye image stabilizers (B) [the compounds shown by the formula (B); the addition amount was shown in Table A] shown in Table A to prepare the emulsified dispersion, samples 102 to 144 were prepared. Each of the samples thus prepared was exposed through an optical wedge and processed by the following steps.

| Processing step | Temperature | Time |
|---|---|---|
| Color Development | 38.5° C. | 45 seconds |
| Blix | 35° C. | 45 seconds |
| Rinse (1) | 35° C. | 30 seconds |
| Rinse (2) | 35° C. | 30 seconds |
| Rinse (3) | 35° C. | 30 seconds |
| Drying | 80° C. | 60 seconds |

[The rinse was a 3 tank countercurrent system of from (3) to (1)]

The compositions of the processing liquids were as follows.

| | |
|---|---|
| [Color Developer] | |
| Water | 800 ml |
| Ethylenediaminetetraacetic Acid | 3.0 g |
| Disodium 4,5-Dihydroxybenzene-1,3-disulfonate | 0.5 g |
| Triethanolamine | 12.0 g |
| Potassium Chloride | 6.5 g |
| Potassium Bromide | 0.03 g |
| Potassium Carbonate | 27.0 g |
| Fluorescent Brightening Agent (Whitex 4, trade name, made by Sumitomo Chemical Company, Limited) | 1.0 g |
| Sodium Sulfite | 0.1 g |
| Disodium-N,N-bis(sulfonatoethyl)hydroxyamine | 5.0 g |
| Sodium Triisopropylnaphthalene(β)sulfonate | 0.1 g |
| N-Ethyl-N-(P-methanesulfonamidoethyl)-3-methyl-4-aminoaniline · 3/2 Sulfuric Acid · monohydrate | 5.0 g |
| Water to make | 1000 ml |
| pH (25° C., adjusted with potassium hydroxide and aqueous ammonia) | 10.00 |
| [Blix Liquid] | |
| Water | 600 ml |
| Ammonium Thiosulfate (750 g/liter) | 93 ml |
| Ammonium Sulfite | 40 g |
| Ethylenediaminetetraacetic acid Iron(III) Ammonium | 55 g |
| Ethylenediaminetetraacetic Acid | 5 g |
| Nitric Acid (67%) | 30 g |
| Water to make | 1000 ml |
| pH (25° C., adjusted with acetic acid and ammonium) | 5.8 |
| [Rinse Liquid] | |
| Chlorinated Sodium Isocyanate | 0.02 g |
| Deionized Water (electric conductivity lower then 5 μs/cm) | 1000 ml |
| pH | 6.5 |

On each of samples 101 to 144 having formed dye images as described above, after measuring the spectral absorption spectrum, each sample was exposed to a xenon tester (illumination 200,000 lux) for 10 days using a ultraviolet absorbing filter (made by Fuji Photo Film Co., Ltd.) cutting the light of the wavelength shorter than 400 nm. The evaluation was carried out by the ratio of the cyan color density=(the density of 650 nm/the density of λMax near 450 nm)×100 as the measure of the color turbidity and by the dye density residual ratio of each sample at the yellow density of 2.0 as the fading inhibition effect.

The measurement was carried out by a Shimazu spectrophotometer and a Fuji automatic densitometer.

The results obtained are shown in Table A.

TABLE A

| Sample | Yellow Coupler | Color Image Stabilizer (amount)*1 | Cyan Density Ratio (%) | Dye Density Residual Ratio (%)*2 | Remarks |
|---|---|---|---|---|---|
| 101 | Y-1 | — | 1.0 | 25 | Comp. Ex. |
| 102 | " | Comp. Compd. a | 3.8 | 10 | " |
| 103 | " | Comp. Compd. b | 1.2 | 16 | " |
| 104 | " | Comp. Compd. c | 2.5 | 38 | " |
| 105 | " | Comp. Compd. d | 1.2 | 32 | " |
| 106 | " | Comp. Compd. e | 3.0 | 37 | " |
| 107 | " | Comp. Compd. f | 2.5 | 39 | " |
| 108 | " | Comp. Compd. g | 3.2 | 35 | " |
| 109 | " | Cpd-2 | 5.0 | 50 | " |
| 110 | " | A-2 | 1.0 | 72 | Invention |
| 111 | " | A-7 | 1.0 | 77 | " |
| 112 | " | A-10 | 1.1 | 70 | " |
| 113 | " | A-16 | 1.1 | 73 | " |
| 114 | Y-3 | — | 0.7 | 16 | Comp. Ex. |
| 115 | " | Comp. Compd. a | 3.0 | 8 | " |
| 116 | " | Comp. Compd. b | 1.0 | 12 | " |
| 117 | " | Comp. Compd. c | 2.3 | 48 | " |
| 118 | " | Comp. Compd. d | 1.0 | 18 | " |
| 119 | " | Comp. Compd. e | 2.3 | 47 | " |
| 120 | " | Comp. Compd. f | 2.1 | 45 | " |
| 121 | " | Comp. Compd. g | 2.9 | 48 | " |
| 122 | " | Cpd-2 | 4.0 | 55 | " |
| 123 | Y-3 | A-2 | 0.8 | 72 | Invention |
| 124 | " | A-7 | 0.7 | 77 | " |
| 125 | " | A-7* | 0.7 | 85 | " |
| 126 | " | A-10 | 0.8 | 75 | " |
| 127 | " | A-20 | 0.9 | 74 | " |
| 128 | " | A-28 | 0.9 | 74 | " |
| 129 | Y-6 | — | 0.8 | 15 | Comp. Ex. |
| 130 | " | Comp. Compd. a | 3.2 | 8 | " |
| 131 | " | Comp. Compd. b | 1.0 | 10 | " |
| 132 | " | Comp. Compd. c | 2.3 | 40 | " |
| 133 | " | Comp. Compd. d | 1.3 | 20 | " |
| 134 | " | Comp. Compd. e | 2.3 | 43 | " |
| 135 | " | Comp. Compd. f | 2.3 | 45 | " |
| 136 | " | Comp. Compd. g | 3.0 | 40 | " |
| 137 | " | Cpd-2 | 4.5 | 50 | " |
| 138 | " | A-2 | 0.8 | 72 | Invention |
| 139 | " | A-7 | 0.8 | 75 | " |
| 140 | " | A-16 | 0.8 | 70 | " |
| 141 | " | A-20 | 0.9 | 75 | " |
| 142 | " | A-2* | 0.8 | 82 | " |
| 143 | Y-7 | A-7 | 0.8 | 78 | " |
| 144 | " | A-7* | 0.8 | 85 | " |

(*): Further, 50 mole % of B-19 was added to the coupler.
(Cpd-2 was same as in Example 3)
Comp. Compd.: Comparative Compound
*1: Addition amount was 50 mole % to the coupler.
*2: Xenon of 200,000 lux, 10 days, the initial density 2.0.

Comparative Compound a

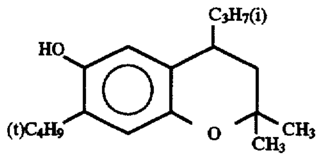

Compound described in JP-B-45-14034

Comparative Compound b

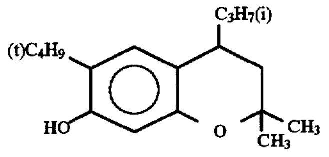

Compound described in WO-91/11749

Comparative Compound c

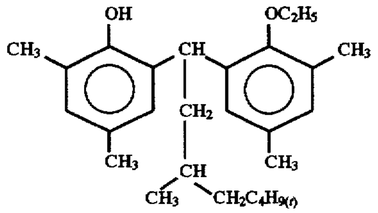

Compound described in JP-A-62-262047, U.S. Pat. No. 4,782,011 and WO-91/08515

Comparative Compound d

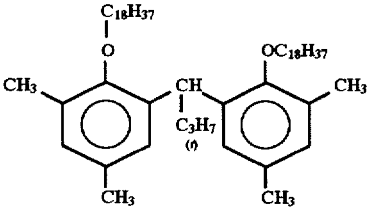

Compound described in JP-A-54-155836

Comparative Compound e

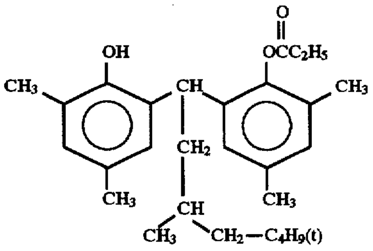

Compound described in JP-A-62-262047 and U.S. Pat. No. 4,782,011

Comparative Compound f

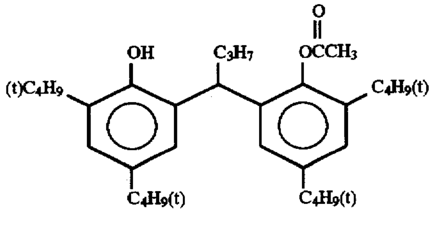

Compound described in JP-A-1-137258

Comparative Compound g

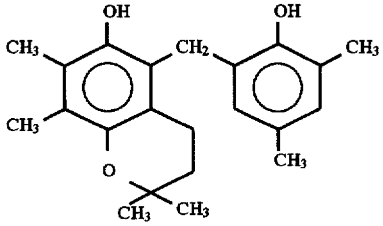

Compound described in JP-A-53-126

From the results shown in Table A, it can be seen that in the case of using the compounds shown by the formula (A) being used in the present invention, the occurrence of the color turbidity is less and the compounds are effective for inhibiting the light fading of color images. Also, it can be seen that the effect of improving the color turbidity and the excellent effect of improving the fastness of the color images have never been anticipated by known techniques. Furthermore, it can be seen that by adding the compound shown by the formula (B), the effect is more improved and the effect is very excellent which is not anticipated by using the compound singly.

EXAMPLE 2

By following the same procedure as in Example 1 except that 11.5 g of a magenta dye-forming coupler M - i was used in place of 16.1 g of the yellow dye-forming coupler and 16.1 g of dibutyl phthalate as the high-boiling organic solvent was changed to 11.5 g, sample 201 was prepared.

Also, by following the same procedure as sample 201 except that in the case of preparing the emulsified dispersion, each of the couplers shown in Table B below (the addition amount is shown in Table B) was coemulsified with each of the color image stabilizer shown in Table B (the addition amount is shown in Table .B) to form each emulsified dispersion, samples 202 to 226 were prepared.

Each of the samples thus obtained was exposed, processed and subjected to the fading test (in this case, however, the xenon lamp exposure dais was 12 days) as in Example 1. The evaluation was carried out by the dye density residual ratio at the initial densities of 0.5 and 1.0 of the samples.

The results obtained are shown in Table B below. In addition, the comparative compounds are same as in Example 1.

TABLE B

| Sample | Magenta Coupler | Dye Image Stabilizer A (amount)*1 | Dye Image Stabilizer B (Amount)*2 | Dye Image Residual Ratio (%)*3 I.D. 0.5 | I.D. 1.0 |
|---|---|---|---|---|---|
| 201 | M-1 | — | — | 3 | 5 |
| 202 | " | C. Compd. a | — | 5 | 5 |
| 203 | " | C. Compd. c | — | 15 | 20 |
| 204 | " | C. Compd. d | — | 15 | 18 |
| 205 | " | C. Compd. f | — | 18 | 20 |
| 206 | " | C. Compd. g | — | 19 | 23 |
| 207 | " | C. Compd. c | B-19 | 28 | 55 |
| 208 | " | C. Compd. g | " | 30 | 54 |
| 209 | " | — | " | 25 | 52 |
| 210 | " | A-7 | — | 55 | 62 |
| 211 | " | A-12 | — | 54 | 60 |
| 212 | " | A-15 | — | 59 | 62 |
| 213 | " | A-7 | B-19 | 68 | 75 |

TABLE B-continued

| Sample | Magenta Coupler | Dye Image Stabilizer A (amount)*1 | Dye Image Stabilizer B (Amount)*2 | Dye Image Residual Ratio (%)*3 | |
|---|---|---|---|---|---|
| | | | | I.D. 0.5 | I.D. 1.0 |
| 214 | " | A-12 | " | 70 | 73 |
| 215 | " | A-15 | " | 73 | 77 |
| 216 | M-10 | — | — | 23 | 42 |
| 217 | " | C. Compd. a | — | 15 | 18 |
| 218 | " | C. Compd. c | — | 28 | 45 |
| 219 | " | C. Compd. e | — | 30 | 47 |
| 220 | " | C. Compd. f | — | 26 | 42 |
| 221 | " | A-2 | — | 53 | 60 |
| 222 | " | A-10 | — | 55 | 62 |
| 223 | " | A-14 | — | 58 | 64 |
| 224 | " | A-2 | B-19 | 72 | 75 |
| 225 | " | A-10 | B-19 | 70 | 73 |
| 226 | " | A-14 | B-19 | 72 | 74 |

C. Compd.: Comparative Compound
*1: Amount was 50 mole % to the coupler
*2: Amount was 100 mole % to the coupler
*3: Xenon lamp of 200,000 lux, 12 days.
I. Density: Initial density Samples 210 to 215 and 221 to 226 are samples of this invention and other samples are comparative samples.

As is clear from the results shown in Table B, it can be seen that the compounds of the present invention are effective for inhibiting light fading the magenta images, and in particular, for the light fading inhibition in a low density regions, and the results show the excellent light fading inhibition effect which has never been anticipated by known compounds.

EXAMPLE 3

A multilayer color photographic paper having the layer constitution shown below (sample 001) was prepared by applying a corona discharging treatment to the surface of a paper support both surfaces of which were laminated with polyethylene, forming a gelatin subbing layer containing sodium dodecylbenzenesulfonate, and coating thereon various photographic layers. In addition, the coating liquids were prepared as follows.

Preparation of Coating Liquid of Layer 1:

In a mixture of 25 g of a solvent (Solv - 1), 25 g of a solvent (Solv - 2), and 180 ml of ethyl acetate were dissolved 153.0 g of a yellow coupler (ExY), 15.0 g of a color image stabilizer (Cpd - 1), and 16.0 g of a color image stabilizer (Solv - 3) and the solution obtained was dispersion by emulsification in 1,000 g of an aqueous 10% gelatin solution containing 60 ml of an aqueous solution of 10% sodium dodecylbenzenesulfonate and 10 g of citric acid to provide emulsified dispersion A.

On the other hand, a silver chlorobromide emulsion A (cubic, a 3:7 (by silver mole ratio) of a large grain size emulsion A having a mean grain size of 0.88 μm and a small grain size emulsion A having a mean grain size of 0.70 μm, the variation coefficients of the grain size distributions of them were 0.08 and 0.10, respectively, in each emulsions, the silver halide grains mainly composed of silver chloride locally had 0.3 mole % silver bromide at a part of the surface) was prepared. The silver chlorobromide emulsion A contained $2.0\times10^{-4}$ mole of each of the blue-sensitive sensitizing dyes A and B shown below in the large grain size emulsion A per mole of silver and $2.5\times10^{-4}$ mole of each of the blue-sensitive emulsions A and B per mole of silver. Also, the silver halide emulsion was chemically sensitized with the addition of a sulfur sensitizer and a gold sensitizer.

The emulsified dispersion A was mixed with the silver chlorobromide emulsion A followed by dissolving to provide the coating liquid for Layer 1 such that the liquid had the composition shown below. In addition, the coated amount of the silver halide emulsion showed the coated amount converted as the amount of silver.

The coating liquids for Layer 2 to Layer 7 were also prepared by the similar manners to the case of preparing the coating liquid for Layer 1.

For each layer, 1-oxy-3,5-dichloro-s-triazine sodium salt was used as the gelatin hardening agent. Also, Cpd - 14 and Cpd - 14 were added to each layer such-that the total amounts thereof became 25.0 mg/m² and 50 mg/m².

In addition, for the silver chlorobromide emulsion for each light-sensitive silver halide emulsion layer, each of the following spectral sensitizing dyes was used.

For Blue-Sensitive Emulsion Layer:

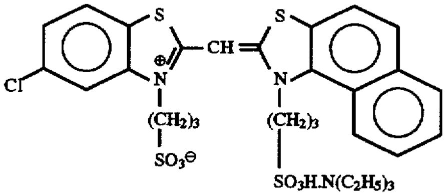

Sensitizing Dye A and

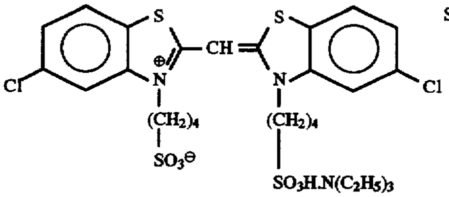

Sensitizing Dye B (each being added to the large grain size emulsion in an amount of $2.0\times10^{-4}$ mole and to the small grain size emulsion in an amount of $2.5\times10^{-4}$ mole per mole of silver halide)

For Green-Sensitive Emulsion Layer:

Sensitizing Dye C

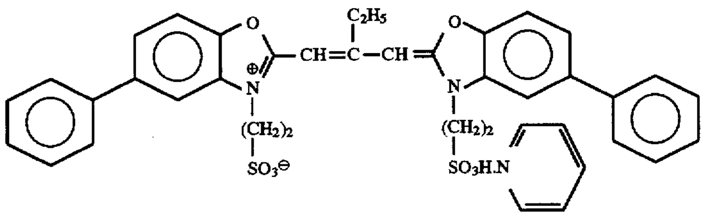

($4.0\times10^{-4}$ mole to the large grain size emulsion and 5.6×–4 mole to the small grain size emulsion per mole of silver halide)

Sensitizing Dye D

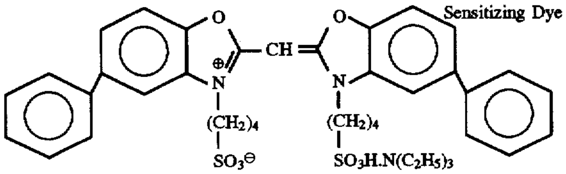

($7.0\times10^{-5}$ mole to the large grain size emulsion and $1.0\times10^{-4}$ mole to the small grain size emulsion per mole of silver halide)

For Red-Sensitive Emulsion Layer:

Sensitizing Dye E

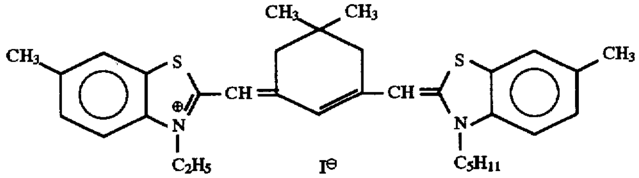

($0.9\times10^{-4}$ mole to the large grain size emulsion and $1.1\times10^{-4}$ mole to the small grain size emulsion per mole of silver halide)

Furthermore, the following compound F was added to the red-sensitive emulsion layer in an amount of $2.6\times10^{-3}$ mole per mole of silver halide.

Compound F

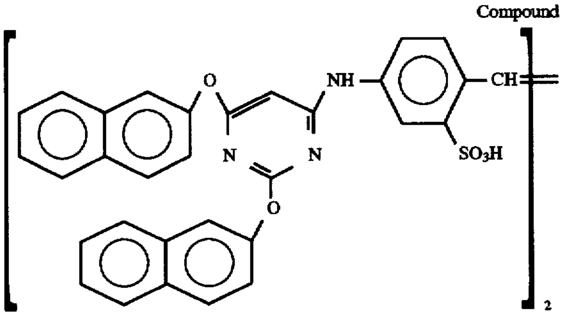

Also, to the blue-sensitive emulsion layer, the green-sensitive emulsion layer, and the red-sensitive emulsion layer was added 1-(5-methylureidophenyl)-5-mercaptotetrzole in the amounts of $8.5\times10^{-5}$ mole, $7.7\times10^{-4}$ mole, and $2.5\times10^{-4}$ mole, respectively, per mole of silver halide, and also to the blue-sensitive emulsion layer and the green-sensitive emulsion layer was added 4-hydroxy-6-methyl-1,1,3a,7-tetraazaindene in the amounts of $1\times10_{-4}$ mole and $2\times10^{-4}$ mole, respectively, per mole of silver halide.

Also, to the silver halide emulsion layers, the following dyes (the numeral in the parenthesis showed the coated amount) were added for the irradiation prevention.

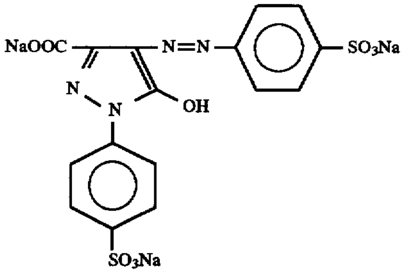

(10 mg/m²)

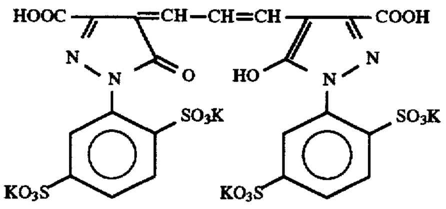

(10 mg/m²)

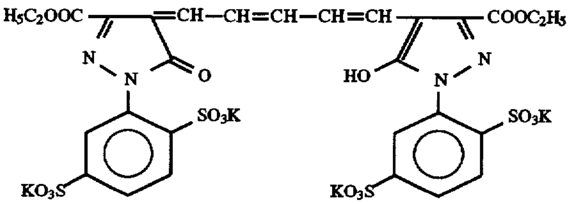

(40 mg/m²)

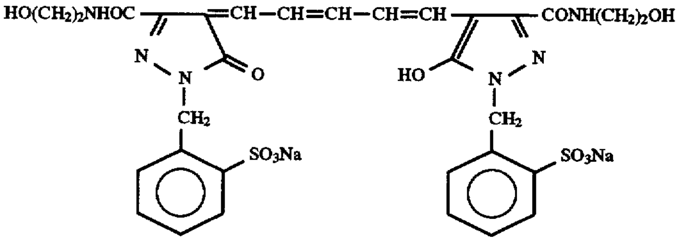

(20 mg/m²)

Layer Structure

Then, the composition of each layer is shown below. The numeral shows the coated amount ($g/m^2$), where in the case of the silver halide emulsion, the numeral shows the silver-converted coated amount.

Support

Polyethylene laminated paper [the polyethylene layer at the side of Layer 1 contained a white pigment ($TiO_2$, 14% by weight) and a bluish pigment (ultramarine)].

| | |
|---|---|
| Layer 1 (Blue-Sensitive Emulsion Layer) | |
| Silver Halide Emulsion A (described above) | 0.27 |
| Gelatin | 1.36 |
| Yellow Coupler (ExY) | 0.79 |
| Color Image Stabilizer (Cpd - 1) | 0.08 |
| Color Image Stabilizer (Cpd - 3) | 0.08 |
| Solvent (Solv - 1) | 0.13 |
| Solvent (Solv - 2) | 0.13 |
| Layer 2 (Color Mixing Inhibition Layer) | |
| Gelatin | 1.00 |
| Color Mixing Inhibitor (Cpd - 4) | 0.06 |
| Solvent (Solv - 7) | 0.03 |
| Solvent (Solv - 2) | 0.23 |
| Solvent (Solv - 3) | 0.25 |

-continued

| | |
|---|---|
| Layer 3 (Green-Sensitive Emulsion Layer) | |
| Silver Chlorobromide Emulsion (cubic, 1:3 mixture (Ag mole ratio) of a large grain size emulsion B having a mean grain size of 0.55 μm and a small grain size emulsion having a mean grain size of 0.39 μm, variation coefficients of the gain size distributions were 0.10 and 0.08, respectively, each emulsion locally had 0.8 mole % AgBr at a part of the surface of grains mainly composed of silver chloride) | 0.13 |
| Gelatin | 1.45 |
| Magenta Coupler (Ex M) | 0.16 |
| Color Image Stabilizer (Cpd - 5) | 0.15 |
| Color Image Stabilizer (Cpd - 2) | 0.03 |
| Color Image Stabilizer (Cpd - 6) | 0.01 |
| Color Image Stabilizer (Cpd - 7) | 0.01 |
| Color Image Stabilizer (Cpd - 8) | 0.08 |
| Solvent (Solv - 3) | 0.50 |
| Solvent (Solv - 4) | 0.15 |
| Solvent (Solv - 5) | 0.15 |
| Layer 4 (Color Mixing Inhibition Layer) | |
| Gelatin | 0.70 |
| Color Mixing Inhibitor (Cpd - 4) | 0.04 |
| Solvent (Solv - 7) | 0.02 |
| Solvent (Solv - 2) | 0.18 |
| Solvent (Solv - 3) | 0.18 |

-continued

| | |
|---|---|
| Layer 5 (Red-Sensitive Emulsion Layer) | |
| Silver Chlorobromide Emulsion (cubic, 1:4 mixture of a large grain size emulsion C having a mean grain size of 0.50 μm and a small grain size emulsion having a mean grain size of 0.14 μm, variation coefficients of the grain size distributions were 0.09 and 0.11, respectively, each emulsion locally had 0.8 mole % AgBr at a part of the surface of the grains mainly composed of silver chloride) | 0.20 |
| Gelatin | 0.85 |
| Cyan Coupler (ExC) | 0.33 |
| Ultraviolet Absorbent (UV - 2) | 0.18 |
| Color Image Stabilizer (Cpd - 1) | 0.33 |
| Color Image Stabilizer (Cpd - 6) | 0.01 |
| Color Image Stabilizer (Cpd - 8) | 0.01 |
| Color Image Stabilizer (Cpd - 11) | 0.01 |
| Solvent (Solv - 6) | 0.22 |
| Color Image Stabilizer (Cpd - 9) | 0.01 |
| Color Image Stabilizer (Cpd - 10) | 0.01 |
| Solvent (Solv - 1) | 0.01 |
| Layer 6 (Ultraviolet Absorption Layer) | |
| Gelatin | 0.55 |
| Ultraviolet Absorbent (UV - 1) | 0.38 |
| Color Image Stabilizer (Cpd - 12) | 0.15 |
| Color Image Stabilizer (Cpd - 5) | 0.02 |
| Layer 7 (Protective Layer) | |
| Gelatin | 1.13 |
| Acryl-Modified Copolymer of Polyvinyl Alcohol (modified degree 17%) | 0.05 |
| Fluid Paraffin | 0.02 |
| Color Image Stabilizer (Cpd - 13) | 0.01 |

The compounds used for preparing the above color photographic paper are shown below.

(ExY) Yellow Coupler

1:1 mixture (by mol ratio) of

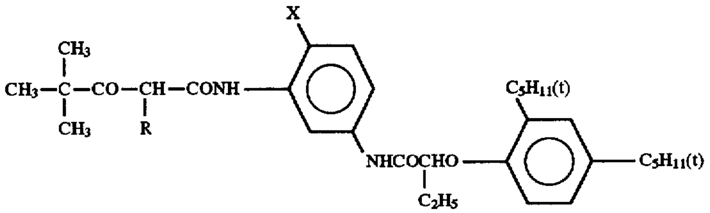

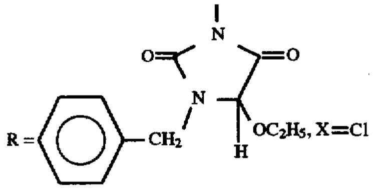

with

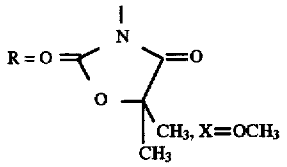

(ExM) Magenta Coupler

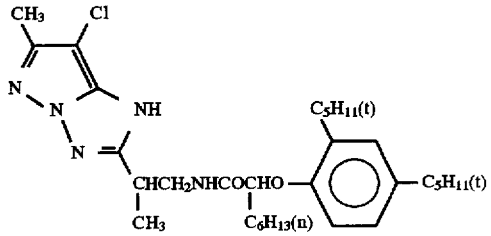

(ExC) Cyan Coupler

2:6 mixture (by mol ratio) of

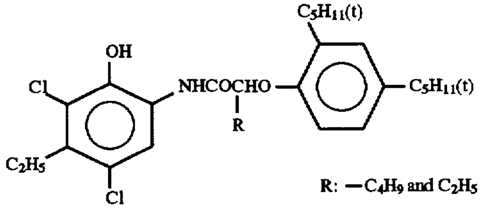

R: $-C_4H_9$ and $C_2H_5$ and

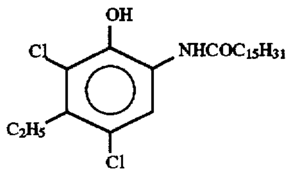

(Cpd - 1) Color Image Stabilizer

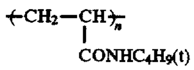

(Cpd - 2) Color Image Stabilizer

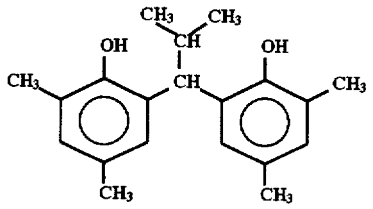

(Cpd-3) Color Image Stabilizer

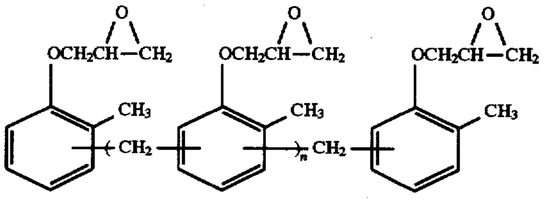

n = 7–8 (average value)

(Cpd-4) Color mixture inhibitor

1:1 mixture (mol ratio) of

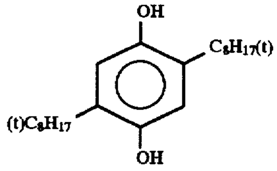

and

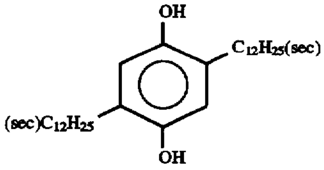

(Cpd-5) Color Image Stabilizer

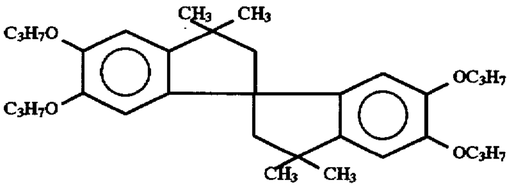

(Cpd-6) Color Image Stabilizer (Cpd-7) Color image Stabilizer

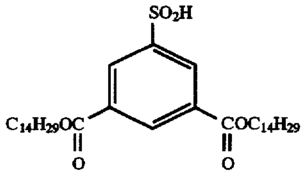

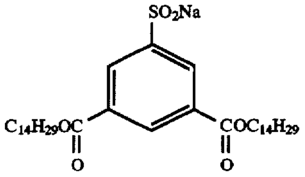

(Cpd-8) Color Image Stabilizer (Cpd-9) Color Image Stabilizer

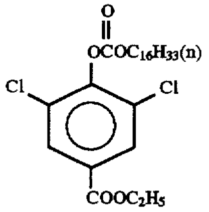

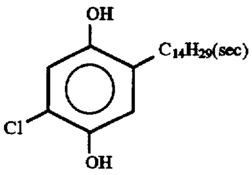

(Cpd-10) Color Image Stabilizer (Cpd-11) Color Image Stabilizer

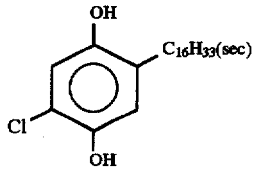

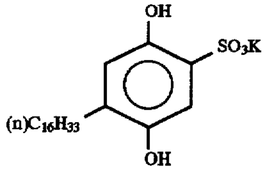

(Cpd-12) Color Image Stabilizer

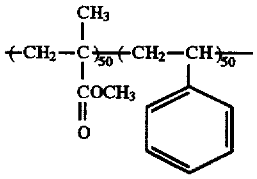

(Cpd-13) Color Image Stabilizer
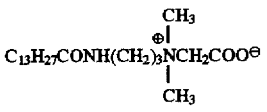
(Cpd-14) Antiseptic agent (Cpd-15) Antiseptic agent
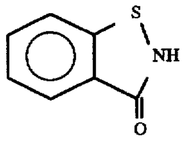
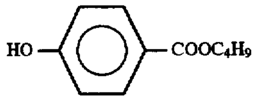
(Solv-1) Solvent (Solv - 2) Solvent
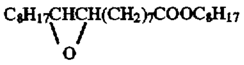
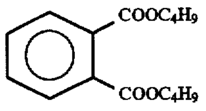
(Solv-3) Solvent
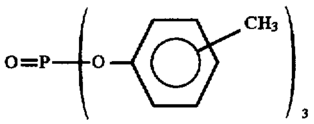
(Solv-4) Solvent
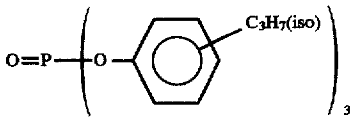
(Solv-5) Solvent
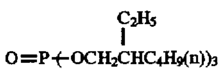
(Solv-6) Solvent
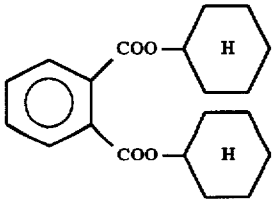
(Solv-7) Solvent
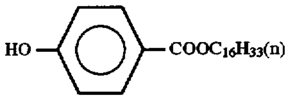
(UV-1) UV Absorbing Agent
5:10:5 mixture (by weight ratio)
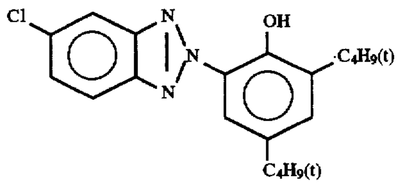
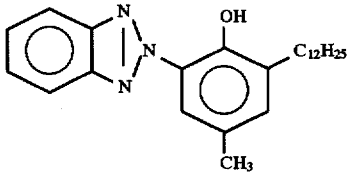
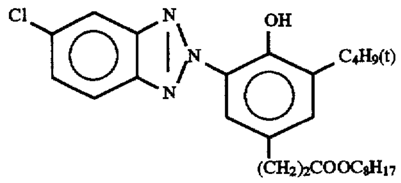
and
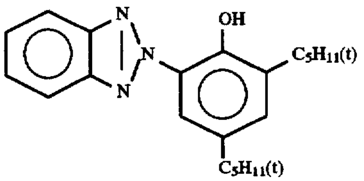
(UV-2) UV Absorbing Agent
1:2:2 mixture (by weight ratio)
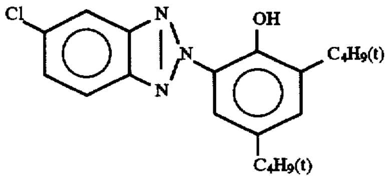
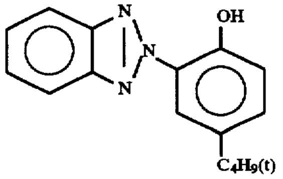
and -continued

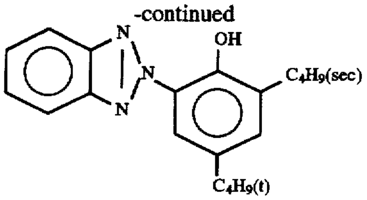

Then, by following the same procedure as the case of preparing sample 001 except that yellow dye-forming coupler ExY or Y - 7 was copolymerized with each of the color stabilizers A and each of the color stabilizes B (added to color image stabilizers Cpd - 1 and Cpd - 3) by the combination as shown in Table C, samples 002 to 010 were prepared. The addition amount of the coupler was the equimolar amount of ExY and the color image stabilizers A and B each was added in an amount of 20 mole % to the yellow coupler. In addition, the comparison compounds are same as in Example 1.

First, sample 001 was subjected to a gray exposure such that about 30% of the coated silver amount was developed using an actinometer (FWH type, manufactured by Fuji Photo Film Co., Ltd., color temperature of the light source 3200° K.). The sample thus exposed was continuously processed using a paper processor and by the following processing steps and the processing liquids having the following compositions, whereby the development processing state under a running equilibrium state was made.

| Processing Step | Temperature | Time (second) | Replenishing Amount* |
|---|---|---|---|
| Color Development | 38.5° C. | 45 | 73 ml |
| Blix | 35° C. | 45 | 60 ml** |
| Rinse (1) | 35° C. | 30 | — |
| Rinse (2) | 35° C. | 30 | — |
| Rinse (3) | 35° C. | 30 | 360 ml |
| Drying | 80° C. | 60 | |

*: The replenishing amount per square meter of the light sensitive material.

The compositions of the processing liquids were as follows.

| | Tank | Replenisher |
|---|---|---|
| Color Developer: | | |
| Water | 800 ml | 800 ml |
| Ethylenediaminetetraacetic Acid | 3.0 g | 3.0 g |
| Disodium 4,5-Dihydtoxybenzene-1,3-dusilfonate | 0.5 g | 0.5 g |
| Triethanolamine | 12.0 g | 12.0 g |
| Potassium Chloride | 6.0 g | — |
| Potassium Bromide | 0.03 g | — |
| Potassium Carbonate | 27.0 g | 27.0 g |
| Fluorescent Brightening Agent (Whitex 4, trade name, made by Sumitomo Chemical Company, ltd.) | 1.0 g | 3.0 g |
| Sodium Sulfite | 0.1 g | 0.1 g |
| Di-Sodium-N,N-bis(sulfonatoethyl)-hydroxylamine | 5.0 g | 10.0 g |
| Sodium Triisopropylnaphthalene(β)-sulfonate | 0.1 g | 0.1 g |
| N-Ethyl-N-(A-methanesulfonamido-ethyl)-3-methyl-4-aminoaniline Sulfate-Monohydrate | 5.0 g | 11.5 g |
| Water to make | 1000 ml | 1000 ml |
| pH (250C, adjusted with potassium hydroxide or sulfuric acid) | 10.00 | 10.00 |

-continued

| | Tank | Replenisher |
|---|---|---|
| Blix Liquid: | | |
| Water | 600 ml | 150 ml |
| Ammonium Thiosulfate (750 g/liter) | 93 ml | 230 ml |
| Ammonium Sulfite | 40 g | 100 g |
| Ethylenediaminetetraacetic Acid | 55 g | 135 g |
| Iron(III) Ammonium Ethylenediaminetetraacetic Acid | 5 g | 12.5 g |
| Nitric Acid (67%) | 30 g | 65 g |
| Water to make | 1000 ml | 1000 ml |
| pH (250C, adjusted with acetic and aqueous ammonia) | 5.8 | 5.6 |
| Rinse Liquid: | Tank Liquid = Replenisher | |
| Chlorinated Sodium Isocyanurate | | 0.02 g |
| De-ionized Water (electric conductivity lower than 5 ps/cm) | | 1000 ml |
| pH | | 6.5 |

Then, each of the samples 001 to 010 was imagewise exposed using a three color separation optical wedge and then processed using the processing liquids described above.

On each sample having dye images thus formed, a fading test was carried out. The evaluation of the fading inhibition effect was carried out be obtaining the yellow dye density residual ratio at the initial density of 2.0 after exposing with a xenon tester (illumination 200,000 lux) for 10 days.

The results obtained are shown in Table C.

TABLE C

| Sample | Coupler | Color Image Stabilizer A (amount)*1 | Color Image Stabilizer B (amount)*1 | Yellow Dye Density Residual Ratio (%)*2 | Remarks |
|---|---|---|---|---|---|
| 001 | ExY | — | — | 23 | Comp. Ex. |
| 002 | " | Comp. Compd. c | — | 42 | " |
| 003 | " | Comp. Compd. c | B-19 | 49 | " |
| 004 | " | A-7 | — | 68 | Invention |
| 005 | " | " | B-19 | 72 | " |
| 006 | Y-7 | — | — | 21 | Comp. Ex. |
| 007 | " | Comp. Compd. c | — | 40 | " |
| 008 | " | Comp. Compd. c | B-19 | 49 | " |
| 009 | " | A-2 | — | 69 | Invention |
| 010 | " | " | B-19 | 80 | " |

*1: The adding amount was 20 mole % to the coupler.
*2: Xenon lamp 200,000 lux, 10 days, initial density 2.0

From the results of Table C, it can be seen that the compounds being used in the present invention show an excellent fading inhibition effect in a multilayer color photographic paper.

Table 4

By following the same procedure as Sample 401 of Example 4 described in JP-A-4-359249 (corresponding to U.S. Pat. No. 5,270,148) except that the coupler (Y - 3) or (Y - 7) was used in place of the coupler in Layer 15, Layer 16, and Layer 17 of Sample 401, and each couple used was copolymerized with the compound (A-2), (A-7), (A-10), (A-20), or (A-28) being used in the present invention in an amount of 25 mole % to the coupler in each layer, samples were prepared.

When each of the samples was exposed and processed as Process 12 of Example 6 described in JP-A-4-359249 and subjected the fading test, the samples of the present invention all showed an excellent fastness and had good photographic characteristics.

Thus, it can be seen that the compounds being used in the present invention show an excellent effect in such a multilayer color photographic material.

EXAMPLE 5

By following the same procedure as the case of preparing the color photographic light-sensitive material of Example 2 described in JP-A-1-158431 except that the coupler (Y - 3) or (Y - 7) being used in the present invention was used in place of the coupler in Layer 11 and layer 12 of the color photographic light-sensitive material and the equimolar amount of the compound (A -2), (A-7), (A-10), (A-16), or (A-20) was used in place of Cpd - 9 in each layer of the color photographic light-sensitive materia, samples were prepared.

When each of the samples was exposed and processed as in Example 2 described in JP-A-1-158431 and the fading resistance (fastness) and the photographic characteristics of these samples thus processed were determined, the samples of the present invention all showed an excellent fastness and had good photographic characteristics.

Thus, it can be seen that the compounds being used in the present invention show an excellent effect in the multilayer color photographic materials.

As described above, according to the present invention, color photographic light-sensitive materials being excellent in the coloring property and giving color images having an excellent fastness can be provided.

While the invention has been described in detail and with reference to specific embodiments thereof, it will be apparent to one skilled in the art that various changes and modifications can be made therein without departing from the spirit and scope thereof.

What is claimed is:

1. A compound represented by formula (A)

(A)

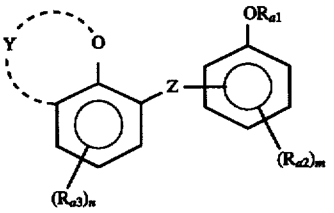

wherein $R_{a1}$ represents a hydrogen atom or an alkyl group having 1 to 40 carbon atoms; $R_{a2}$ represents an aliphatic group having 1 to 16 carbon; $R_{a3}$ represents an aliphatic group having 1 to 16 carbon atoms; Y represent non-metallic atomic group necessary for completing a coumaran or chroman ring, an oxygen atom, a sulfur atom, or $—C(R_{a4})(R_{a5})—$, wherein $R_{a4}$ and $R_{a5}$, which may be the same or different, each represents a hydrogen atom or an aliphatic group having 1 to 16 carbon atoms; m represents an integer of from 0 to 4; n represents an integer of from 0 to 3; when m is 2 or more, plural $R_{a2}$'s may be the same or different; and when n is 2 or more, plural $R_{a3}$'s may be the same or different.

2. The compound as claimed in claim 1 wherein said compound is a compound represented by formula (A-1)

(A-1)

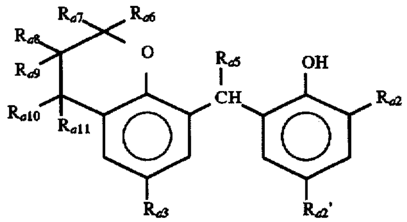

wherein $R_{a2}$, $R_{a3}$ and $R_{a5}$ have the same meaning as defined for formula (A), $R_{a2'}$ has the same meaning as $R_{a2}$, and $R_{a6}$, $R_{a7}$, $R_{a8}$, $R_{a9}$, $R_{a10}$, and $R_{11}$, which may be the same or different, each represents a hydrogen atom or an alkyl group having 1 to 10 carbon atoms.

3. The compound as claimed in claim 2, wherein $R_{a2}$ and $R_{a2'}$ each represents a methyl group, $R_{a3}$ is a methyl group, $R_{a5}$ is a methyl group or an i-propyl group, and $R_{a6}$, $R_{a7}$, $R_{a8}$, $R_{a9}$, $R_{a10}$ and $R_{a11}$ each represents a hydrogen atom, a methyl group or i-propyl group.

4. The compound as claimed in claim 2, wherein $R_{a2}$ and $R_{a2'}$ each represent a methyl group.

5. The compound as claimed in claim 2, wherein $R_{a5}$ is a methyl group or an iso-propyl group.

6. The compound as claimed in claim 2, wherein $R_{a6}$, $R_{a7}$, $R_{a8}$, $R_{a9}$, $R_{a10}$ and $R_{a11}$ are each independently selected from the group consisting of a hydrogen atom, a methyl group, and an iso-propyl group.

* * * * *